United States Patent
Rother et al.

(10) Patent No.: US 10,465,211 B2
(45) Date of Patent: Nov. 5, 2019

(54) LYASE AND METHOD FOR ASYMMETRIC SYNTHESIS OF (S)-PHENYLACETYLCARBINOL

(71) Applicant: Forschungszentrum Juelich GmbH, Juelich (DE)

(72) Inventors: Doerte Rother, Huerth (DE); Martina Pohl, Aachen (DE); Torsten Sehl, Offenburg (DE); Lisa Marx, Seeheim-Jugenheim (DE); Robert Westphal, Leipzig (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days.

(21) Appl. No.: 15/511,331

(22) PCT Filed: Aug. 27, 2015

(86) PCT No.: PCT/DE2015/000435
§ 371 (c)(1),
(2) Date: Mar. 15, 2017

(87) PCT Pub. No.: WO2016/041535
PCT Pub. Date: Mar. 24, 2016

(65) Prior Publication Data
US 2017/0260550 A1 Sep. 14, 2017

(30) Foreign Application Priority Data
Sep. 16, 2014 (DE) .......................... 10 2014 013 642

(51) Int. Cl.
*C12N 9/88* (2006.01)
*C12N 15/60* (2006.01)
*C12P 7/26* (2006.01)
*C12P 7/22* (2006.01)

(52) U.S. Cl.
CPC .................. *C12P 7/26* (2013.01); *C12N 9/88* (2013.01); *C12Y 401/01001* (2013.01)

(58) Field of Classification Search
None
See application file for complete search history.

(56) References Cited

U.S. PATENT DOCUMENTS

| | | |
|---|---|---|
| 5,789,166 A | 8/1998 | Bauer et al. |
| 5,932,419 A | 8/1999 | Bauer et al. |
| 6,391,548 B1 | 5/2002 | Bauer et al. |
| 10,006,061 B2 * | 6/2018 | Rother ..................... C12N 9/88 |

OTHER PUBLICATIONS

Westphal et al., "A Tailor-Made Chimeric Thiamine Diphosphate Dependent Enzyme for the Direct Asymmetric Synthesis of (S)-Benzoins", Angew. Chem. Int. Ed. 53:976-9379, first published Jul. 2014 (Year: 2014).*
Hailes et al., FEBS J. 280:6374-6394, Sep. 13, 2013 (Year: 2013).*
Siegert et al., Prot. Eng. Des. Sel. 18:345-357, 2005 (Year: 2005).*
Waldemar Adam, et al., "Synthesis of Optically active α-Hydroxy Carbonyl compoiunds by the Catalytics, Enantioselective Oxidation of Silyl Enol Ethers and Ketene Acetals with (Salen)manganese(III) Complexes", J. Am. Chem. Soc., Dec. 1998, vol. 120, pp. 708-714.
J. Brussee, et al., "Bio.Organic Syntehsis of Optically Active Cyanhydrins and Acyloins", Tetrahedron Letters, vol. 29, No. 35, pp. 4485-4488, Dec. 1988.
Franklin A. Davis, et al., "Influence of Enolate Geometry and Strucutre on the Stereochemistry of the Asymmetric Oxidation of Prochiral Ketone Enolates to Optically Active α-Hydroxy Ketones", Tetrahedron Letters, vol. 30, No. 7, pp. 779-782, Dec. 1989.
Dörte Gocke, et al., "Rational Protein Design of ThDP-Dependent Enzymes: Engineering Stereoselectivity", ChemBioChem, vol. 9, Issue 3, Feb. 15, 2008, pp. 406-412.
D. Gocke, et al., "Rationales Enzymdesign für die (S)-selektive Benzoinkondensation", Chemie Ingenieur Technik, vol. 81, No. 8, Dec. 2009.
Robert Westpahl, et al., "A Tailor-Made Chimeric Thiamine Diphosphate Dependent Enzyme for the Direct Asymmetric Synthesis of (S)-Benzoins", Anges. Chem. Int., Ed., Dec. 2014, vol. 53, pp. 9376-9379.
Dörte Rother, et al., "S-Selective Mixed Carboliation by Structure-Based Design of the Pyruvate Decarboxylase from Acetobacter pasteurianus", ChemCatChem, vol. 3, Dec. 2011, pp. 1587-1596.
Steven A. Fleming, et al., "Asymmetric dihydroxylation of allenes", Tetrahedron Letters, vol. 45, Dec. 2004, pp. 3341-3343.
Torsten Sehl, et al., "Efficient 2-step biocatalytic strategies for the synthesis of all nor(pseudo)ephedrine isomers", Green Chem., vol. 16, pp. 3341-3348, Dec. 2014.
Tina Gerhards, et al., "Influence of Organic Solvents on Enzymatic Asymmetric Carboligations", Adv. Synth. Catal., vol. 354, Oct. 4, 2012, pp. 2805-2820.
Esa Toukoniitty, et al., "Enantioselective Hydrogenation of 1-Pheynl-1, 2-propanedione", Journal of Catalysis, vol. 204, Dec. 2001, pp. 281-291.
Waldemar Adam, et al., "Asymmetric C-H Oxidation of vic-Diols to α-Hydrocy Ketones by a Fructos4e-Derived Dioxirane: Electronic Effects on the Enantioselectivity of Oxygen Transfer", J. Org. Chem., vol. 64, Dec. 1999, pp. 7492-7497.
Zi-Qiang Rong, et al., "Enantioselective Oxidation of 1,2-Diols with Quinine-Derived Urea Organocatalyst", Org. Lett., vol. 16, Dec. 2014, pp. 208-211.
Torsten Sehl et al: "Asymmetric synthesis of (S)-phenylacetylcarbinol—closing a gap in C-C bon formation", Journal of Immunotherapy, vol. 19, Jan. 26, 2017, pp. 380-384, XP009508211.

* cited by examiner

*Primary Examiner* — David Steadman
(74) *Attorney, Agent, or Firm* — Leydig, Voit & Mayer, Ltd.

(57) ABSTRACT

A lyase has an amino acid sequence selected from SEQ ID NOs: 1, 2 and 3, wherein the amino acid isoleucine in position no. 468 in the protein ApPDC-E469G, which is modified with respect to the wild type from *Acetobacter pasteurianus*, is replaced by an amino acid which occupies less space than isoleucine.

20 Claims, 1 Drawing Sheet
Specification includes a Sequence Listing.

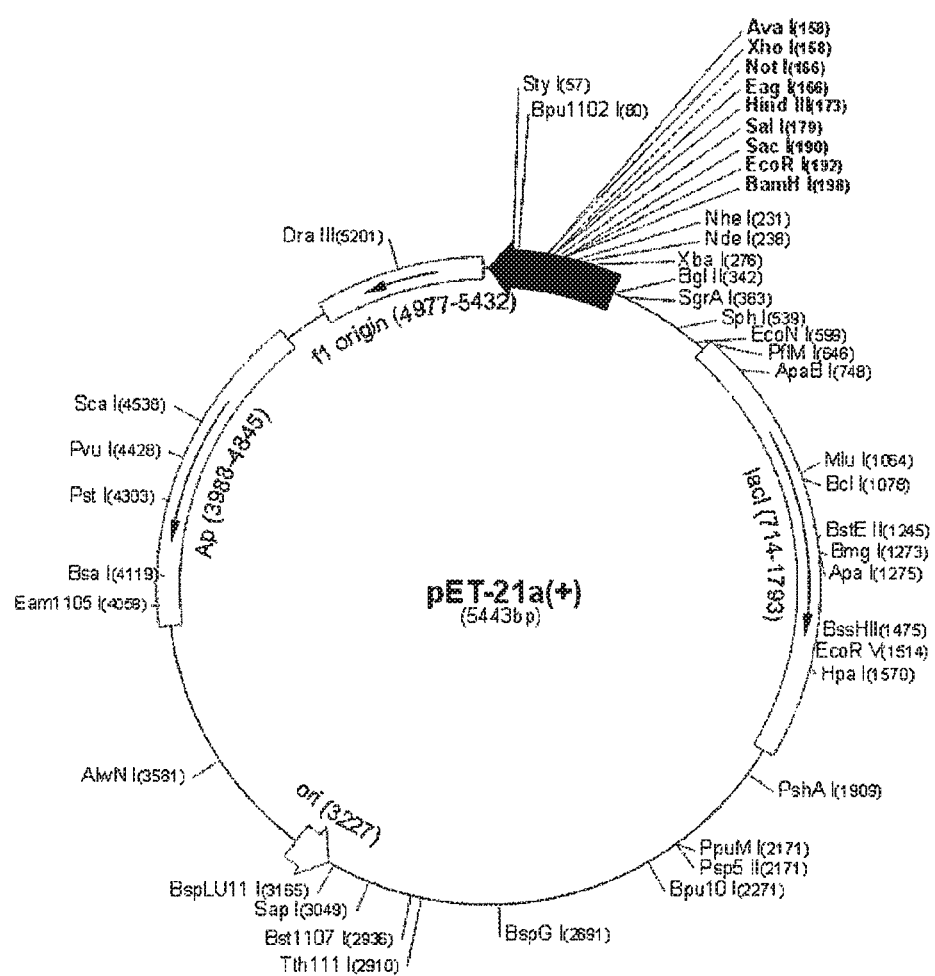

LYASE AND METHOD FOR ASYMMETRIC SYNTHESIS OF (S)-PHENYLACETYLCARBINOL

CROSS REFERENCE TO PRIOR APPLICATIONS

This application is a U.S. National Phase application under 35 U.S.C. § 371 of International Application No. PCT/DE2015/000435, filed on Aug. 27, 2015, and claims benefit to German Patent Application No. DE 10 2014 013 642.6, filed on Sep. 16, 2014. The International Application was published in German on Mar. 24, 2016 as WO 2016/041535 A1 under PCT Article 21(2).

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 238,176 bytes ASCII (Text) file named "815662_ST25.txt," created Mar. 6, 2017.

FIELD

The invention relates to a lyase and to a method for asymmetric synthesis of (S)-phenylacetylcarbinol.

BACKGROUND (S)-Phenylacetylcarbinol is a valuable chiral building block in organic syntheses and can be used for synthesis of fine chemicals and pharmaceuticals. According to the prior art to date no methods are known in which (S)-phenylacetylcarbinol (S)-PAC can be generated in optical purities of >89% ee by asymmetric synthesis from non-chiral, inexpensive compounds. However, high optical purities are of decisive importance in the production of fine chemicals or pharmaceuticals.

According to the prior art, various methods are known for producing (S)-phenylacetylcarbinol.

On the one hand chemical syntheses are known.

The methods for producing (S)-PAC based on chemical asymmetric synthesis generate an ee of 68% or 86%. The methods are described in the publications of Davis, Franklin A.; Sheppard, Aurelia C; Lal, G. Sankar Tetrahedron Letters, 1989, vol. 30, 7 p. 779-782 and Adam, Waldemar; Fell, Rainer T.; Stegmann, Veit R.; Saha-Moeller, Chantu R. Journal of the American Chemical Society, 1998, vol. 120, 4 p. 708-714. There are furthermore methods in which (S)-PAC is formed only as a by-product and (R)-PAC is present in an enantiomeric excess, such as for example in the following reactions, such as the reduction of 1-phenylpropane-1,2-dione, which is described in the publications of Toukoniitty, Esa; Maeki-Arvela, Paeivi; Kuzma, Marek; Villela, Alexandre; Kalantar Neyestanaki, Ahmad; Salmi, Tapio; Sjoeholm, Rainer; Leino, Reko; Laine, Ensio; Murzin, Dmitry Yu, Journal of Catalysis, 2001, vol. 204, 2 p. 281-291, and the synthesis starting from benzaldehyde, which is described by Fleming, Steven A.; Carroll, Sean M.; Hirschi, Jennifer; Liu, Renmao; Pace, J. Lee; Redd, J. Ty Tetrahedron Letters, 2004, vol. 45, 17 p. 3341-3343, and the reaction of 2-hydroxy-2-phenylacetonitrile of Brussee, J.; Roos, E. C; Gen, A. Van Der Tetrahedron Letters, 1988, vol. 29, 35 p. 4485-4488.

A synthesis is moreover described in which the chiral building block 1-phenylpropane-1,2-diol can be oxidized to (S)-PAC. (S)-PAC is formed with an enantiomeric excess of 91%, as described by Zi-Qiang Rong, Hui-Jie Pan, Hai-Long Yan, and Yu Zhao Organic Letters, 2014, 16 (1), pp 208-211, or 69%, as has been described by Waldemar Adam, Chantu R. Saha-Moeller, and Cong-Gui Zhao Journal of Organic Chemistry, 64(20), 7492-7497; 1999, but in addition is contaminated with a regioisomer which must be separated off in a cumbersome manner.

An enzymatic asymmetric synthesis is furthermore known, which is described in the 2013 dissertation of Alvaro Gómez Baraibar entitled "Development of a biocatalytic production process for (S)-alpha-hydroxy ketones". If this enzyme expressed according to this dissertation heterologously in Escherichia coli is used for the synthesis in whole cells, the optical purity of (S)-PAC is ~43% ee.

This only enzymatic asymmetric synthesis of (S)-PAC was described in a carboligation reaction starting from benzaldehyde and acetaldehyde, or benzaldehyde and pyruvate. The reaction is catalyzed by a variant of the enzyme pyruvate decarboxylase from Acetobacter pasteurianus, ApPDC-E469G, in which in position no. 469 glutamate is replaced by glycine. The highest enantiomeric excess which has been achieved with the isolated enzyme in this context is 89%, as described by Rother Nee Gocke, Doerte; Kolter, Geraldine; Gerhards, Tina; Berthold, Catrine L.; Gauchenova, Ekaterina; Knoll, Michael; Pleiss, Juergen; Mueller, Michael; Schneider, Gunter; Pohl, Martina in the publication in ChemCatChem, 2011, vol. 3, 10 p. 1587-1596.

SUMMARY

In an embodiment, the present invention provides a lyase comprising an amino acid sequence according to SEQ ID NOs: 1, 2 or 3, wherein the amino acid isoleucine in position no. 468 in the protein ApPDC-E469G, which is modified with respect to the wild type from Acetobacter pasteurianus, is replaced by an amino acid which occupies less space than isoleucine.

BRIEF DESCRIPTION OF THE DRAWINGS

FIG. 1 shows a plasmid according to an embodiment of the invention (pET-21a(+) vector map).

DETAILED DESCRIPTION

In an embodiment the present invention provides an alternative enzymatic method for the asymmetric synthesis of (S)-phenylacetylcarbinol which renders possible a high enantiomeric excess of (S)-phenylacetylcarbinol. In a production with whole cells, the enantiomeric excess is to be greater than 43%.

Furthermore, no by-products and no regioisomers are to be formed. It is to be possible in this context to employ inexpensive educts which are not chiral. An asymmetric synthesis of (S)-phenylacetylcarbinol is to be rendered possible. Expensive separation of chiral product mixtures is to be prevented.

An enzyme with which (S)-phenylacetylcarbinol can be produced from benzaldehyde and pyruvate or acetaldehyde and a DNA encoding the enzyme are to be provided.

Furthermore, a method for producing the enzyme is provided.

A method for producing (S)-phenylacetylcarbinol which also renders possible high enantiomeric excesses when crude cell extracts or whole cells are employed is to be provided.

Certain embodiments of the invention provide a variant of the lyase ApPDC-E469G in which the isoleucine in position no. 468 is replaced by an amino acid which occupies a reduced space with respect to isoleucine. These lyases are employed according to other embodiments for reacting benzaldehyde with pyruvate or acetaldehyde to give (S)-phenylacetylcarbinol.

With these embodiments, it is now possible to produce (S)-phenylacetylcarbinol of 93% ee using whole cells and of 85% ee using a crude cell extract. No by-products, in particular no regioisomers are formed. As a result of the synthesis being carried out with non-chiral educts, it is inexpensive. Separation of enantiomers can be dispensed with. High enantiomeric excesses can also be achieved in the production of (S)-phenylacetylcarbinol with crude cell extracts or whole cells.

According to an embodiment of the invention, a lyase is provided in which the isoleucine in position no. 468 in the protein ApPDC-E469G, which is modified with respect to the wild type from *Acetobacter pasteurianus*, is replaced by an amino acid which takes up less space than isoleucine.

This lyase has a positive influence on the increase in the stereoselectivity in the production of (S)-phenylacetylcarbinol.

The following lyases which meet this requirement may be mentioned as preferred:

ApPDC-E469G-I468G according to SEQ ID NO: 1 with glycine in position no. 468

ApPDC-E469G-I468A according to SEQ ID NO: 2 with alanine in position no. 468

ApPDC-E469G-I468V according to SEQ ID NO: 3 with valine in position no. 468

To improve the enantiomeric excess, the enzymes ApPDC-E469G-I468L, ApPDC-E469G-I468T, ApPDC-E469G-I468C or ApPDC-E469G-I468S can be employed in the production of (S)-phenylacetylcarbinol.

Deoxyribonucleic acids which encode the enzymes mentioned are furthermore provided according to certain embodiments of the invention.

According to an embodiment of the invention, these are deoxyribonucleic acids which encode a variant of the enzyme ApPDC-E469G and which in position no. 1402 to 1404 encode an amino acid which occupies a reduced space with respect to isoleucine.

For the example according to SEQ ID NO: 1, in which in this position the amino acid glycine is encoded, the nucleic acids GGT, for example, can be in positions no. 1402-1404.

By way of example, a deoxyribonucleic acid encoding the enzyme ApPDC-E469G-I468G with glycine in position no. 468 according to SEQ ID NO: 1 is described according to SEQ ID NO: 4.

For the enzymes according to embodiments of the invention, ApPDC-E469G-I468A according to SEQ ID NO: 2 with alanine in position no. 468 and ApPDC-E469G-I468V according to SEQ ID NO: 3 with valine in position no. 468, the deoxyribonucleic acids encoding these can be provided by replacement of the corresponding nucleotides in position no. 1402-1404.

A DNA encoding the enzymes according to certain embodiments of the invention can be produced by directed or non-directed mutagenesis by methods known to a person skilled in the art. Directed mutagenesis is preferred in this context. These methods are known to a person skilled in the art. An example of producing an embodiment of the invention is disclosed concretely in the specific description part. This procedure can also be employed in principle for all the other deoxyribonucleic acids and enzymes disclosed, so that all the enzymes and deoxyribonucleic acids according to the invention can be produced by an analogous route.

The deoxyribonucleic acids can be ligated into a vector, preferably a plasmid.

Empty vectors which can be employed are, for example, pET-20b(+), pET-21a-d(+), pET-22b(+), pET-23a-d(+), pET-24a-d(+), pET-25b(+), pET-26b(+), pET-27b(+), pET-28a(+), pET-29a-c(+), pET-30a-c(+), pET-31b(+), pET-34b(+), pET-35b(+), pET-36b(+), pET-37b(+), pET-38b(+), into which the corresponding DNAs according to the invention are ligated.

Alternatively, the deoxyribonucleic acids can also be ligated into the genome.

The ligated deoxyribonucleic acids are DNA sequences which encode a variant of the enzyme ApPDC-E469G and which in position no. 1402-1404 encode an amino acid which occupies a reduced space with respect to isoleucine. The deoxyribonucleic acids can also encode the enzymes ApPDC-E469G-I468L, ApPDC-E469G-I468T, ApPDC-E469G-I468C or ApPDC-E469G-I468S.

Preferably, the ligated deoxyribonucleic acid encodes the proteins according to SEQ ID NOs: 1, 2 and 3.

According to certain embodiments of the invention, vectors can be provided which contain a deoxyribonucleic acid which encodes a variant of the enzyme ApPDC-E469G and which in position no. 1402-1404 encode an amino acid which occupies a reduced or the same space with respect to isoleucine.

Preferably, the vector contains a deoxyribonucleic acid according to SEQ ID NO: 4.

Preferably, the vector is a plasmid.

SEQ ID NO: 5 shows by way of example a DNA sequence for a plasmid according to the invention which contains a DNA according to SEQ ID NO: 4.

According to an embodiment of the invention, benzaldehyde is reacted with pyruvate or with acetaldehyde according to formula (1) by means of a variant of the enzyme ApPDC-E469G, which has in position no. 468 an amino acid which occupies a reduced space with respect to isoleucine, preferably an enzyme from the group according to SEQ ID NO: 1, 2 or 3, to give (S)-phenylacetylcarbinol.

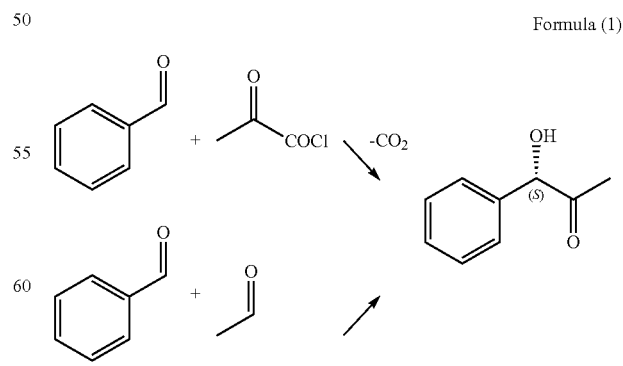

Formula (1)

The reaction is preferably carried out in aqueous solution.
The pH is in a range of 5-9, preferably 6.5-8, particularly preferably 6.5-7.

In this reaction, potassium phosphate buffer, HEPES, MOPS, TEA or TRIS-HCl, for example, can be employed as a buffer.

Thiamine diphosphate and magnesium sulfate can furthermore be employed as cofactors.

The reaction can be carried out in vivo or in vitro.

For the in vivo production of (S)-phenylacetylcarbinol, for example, *E. coli*, a *Corynebacterium*, for example *Corynebacterium glutamicum*, or a yeast, such as *Saccharomyces cerevisiae*, can be employed as the production organism.

For this, the production organisms are transformed with the DNA according to an embodiment of the invention or a vector which contains the DNA.

The DNA can also be introduced into the genome in the production organism.

The genes employed are expressed heterologously in this context.

For the in vitro production, either the isolated enzyme or the cell extract of the production organisms can be employed.

Typical temperatures are between 20° C. and 40° C., 20° C. to 30° C. are preferred and a temperature of from 20° C. to 25° C. is particularly preferred.

The reaction times can be 2 h-48 h, preferably 6 h-24 h, particularly preferably 12 h.

Some examples, which are not to be interpreted as limiting, are described in the following.

The reactions can be carried out in a conventional set-up in a reaction flask with stirring.

In order to be able to produce (S)-PAC in high enantiomeric excesses, a variant of the enzyme ApPDC-E469G was produced by mutagenesis. The variant ApPDC-E469G-I468G produces (S)-PAC using the crude cell extract enzymes with an ee of 85%. Using ApPDC-E469G-I468G, which was expressed heterologously in *Escherichia coli* and is employed as an inexpensive whole cell catalyst, (S)-PAC with an ee of 93% can be generated.

Example 1

20 mM benzaldehyde, 400 mM pyruvate, 2.5 mM magnesium sulfate, 100 μM thiamine diphosphate, 20 mg/ml (moist weight) of ApPDC-E469G-I468G (whole cells of *E. coli* in which ApPDC-E469G-I468G was expressed), 50 mM potassium phosphate butter pH 6.5, 25° C., reaction time: 48 h.

Enantiomeric purity of (S)-PAC: ee 93%
Yield: 67%.

Example 2

20 mM benzaldehyde, 400 mM pyruvate, 2.5 mM magnesium sulfate, 100 μM thiamine diphosphate, 1 mg/ml of ApPDC-E469G-I468G (crude cell extract of *E. coli* cells in which ApPDC-E469G-I468G was expressed), 50 mM potassium phosphate buffer pH 6.5, 25° C., reaction time: 48 h.

Enantiomeric purity of (S)-PAC: ee 85%

The production of the enzymes according to certain embodiments of the invention and of the deoxyribonucleic acids encoding them is explained by way of example in the following. The method described can also be employed analogously in principle for the production of the other lyases according to the invention and the deoxyribonucleic acids encoding them.

Production of the DNA of the Enzyme Variant ApPDC-E469G-I468G
Site Saturated Mutagenesis The method of site saturated mutagenesis according to the variant of Reetz et al. (Reetz, Kahakeaw et al. 2008) was carried out starting from the gene sequence ApPDC-E469G (template DNA) in order to obtain amino acid replacements at position no. 1468. NDT codons which encode 12 out of 20 natural amino acids are used in this method.

Polymerase Chain Reaction (PCR)

In an initial step, the template DNA is multiplied by means of the polymerase chain reaction (PCR) and at the same time mutations are introduced here by using degenerated primers and NDT codons. The primers used were obtained from "Eurofins MWG Operon" (see eurofins genomics website) and had the following sequence:

Primers for Site Saturated Mutagenesis for Producing ApPDC-E469G-I468NDT

```
forward:
                                         (seq. no. 6)
5' CCGTGGCTATGTCNDTGGCATCGCCATTC 3' reverse:
                                         (seq. no. 7)
5* GAATGGCGATGCCAHNGACATAGCCACGG 3'
```

A master solution was first prepared and then divided into four batches of 50 μl each. To start the reaction, 1 μl of KOD Hot Start Polymerase was added.

PCR Reaction Batch:
1 portion of PCR buffer
5% (v/v) of DMSO
2 mM MgSO$_4$
0.2 mM nucleotides
0.25 pmol of forward primer
0.25 pmol of reverse primer
0.1 ng/μl of DNA template The reaction was carried out under the following conditions:

| | Duration (min) | Temperature (° C.) | Repetitions |
|---|---|---|---|
| Initialization | 2:00 | 95 | |
| Denaturing | 2:00 | 95 | |
| Annealing | 1:00 | 75.5 | 20x |
| Elongation | 6:00 | 70 | |
| Termination | 10:00 | 70 | |

To digest the template DNA, 1 μl of the enzyme DpnI (Eppendorf) was added to the solution and the batch was incubated at 37° C. for 1 h. The entire batch was then purified with the DNA Purification Kit (list of chemicals) before the further transformation.

Transformation of *E. coli* BL21-DE3 and *E. coli* DH5α

The strains *E. coli* BL21-DE3 and *E. coli* DH5α were transformed with the DNA produced by site saturation mutagenesis. For this, 100 ng of the DNA were added to 50 μl of competent cells and the batch was incubated on ice for 30 min. A heat shock was then carried out at 42° C. for 90 sec. After 3 min on ice, 500 μl of SOC medium were added and the solution was then incubated in an Eppendorf Thermomixer at 350 rpm and 37° C. for 45 min. After the incubation had been carried out, the cell suspension was centrifuged at 13,000 rpm in an Eppendorf bench centrifuge for 30 sec and the pellet was then resuspended in 100 μl of supernatant. The cell suspension, which had been concentrated to 100 µl, was plated out on LB agar plates (with 100 µg/ml of ampicillin) and incubated upside-down at 37° C. for 16 h.

Expression of the Enzyme Variants 46 individual colonies of the transformation were picked from the plate with a toothpick and were each incubated in a well of a 48-well Nerbe plate (Nerbe Plus GmbH) with 1 ml each of LB medium at 20° C. and 850 rpm for 24 h (master plate). A further well was inoculated with E. coli BL21-DE3 cells which had been transformed analogously beforehand with the ApPDC-E469G template DNA. After the incubation had been carried out 10 µl of the cell suspensions were added to in each case 1.5 ml of autoinduction medium in 48-well FLOWERPLATES (m2p-labs, Germany; 48-well microtiter plate). The FLOWERPLATE was incubated at 20° C. and 850 rpm for 48 h. 300 µl of glycerol was added to the remaining volume (990 µl) of the master plate and the mixture was stored at −80° C.

Cell Breakdown and Carboligation

The variants expressed in the FLOWERPLATES (m2p-labs, Germany; 48-well microtiter plate) were broken down by freezing (48 h, 4° C.). After re-thawing, 500 µl portions of the cell suspensions were transferred into two wells of a 96-well plate (duplicate determination). The plate was centrifuged at 4,000 rpm for 3 min and the pellet was resuspended in 420 µl of KPi buffer with 1 mg/ml of lysozyme. The plate was incubated at 20° C. and 400 rpm for 1 h and then centrifuged again at 4,000 rpm for 10 min. 250 µl portions of the supernatant were each pipetted into a well of a 2 ml Nerbe plate and 250 µl of a reaction solution of 40 mM benzaldehyde, 400 mM pyruvate, 4 mM magnesium sulfate and 400 µM thiamine diphosphate were added. The plate was incubated again for 24 h and the reaction solutions were then analyzed (see HPLC analysis).

HPLC Analysis

In each case 200 µl of heptane were added to 200 µl of the carboligation reaction solutions, the mixtures were vortexed and 150 µl portions of the upper phase were then transferred into HPLC vials. The samples were analyzed with a Chiralpak IC-3 column (Chiral Technologies Inc.) using the following method.

HPLC Program

| Length | 24 min |
| Flow rate | 0.5 ml/min |
| Mobile phase | 25% isopropanol |
|  | 75% heptane |

Typical Retention Times and Wavelength Used for the Quantification

|  | Retention time (min) | Wavelength (nm) |
| --- | --- | --- |
| (R)-PAC | 12.3 | 210 |
| (S)-PAC | 12.9 | 210 |
| Benzaldehyde | 11.4 | 254 |

DNA isolation and identification of the best enzyme variants by DNA sequencing The DNA of the enzyme which gave the highest ee values for (S)-PAC in the carboligation reactions was sequenced starting from the master plate for identification of the mutation. For this cells were first transferred with an inoculation loop from the master plate to which glycerol had been added into 50 ml of LB medium (+50 µg/ml of ampicillin) and the mixture was incubated at 37° C. in a 250 ml conical flask. After incubation for 12 h, 20 ml of the cell suspension were centrifuged (4,000 rpm, 5 min, 4° C.). The DNA of the cells in the pellet was isolated by the method of the QIAprep® Spin Miniprep Kit analogously to the manufacturers instructions (Qiagen N.V.). In addition the concentration of the DNA was adjusted to 100 ng/µl and the DNA was sequenced by LGC Genomics GmbH.

LB (Lysogeny Broth) Medium

| 10 g/l | NaCl |
| 10 g/l | peptone |
| 5 g/l | yeast extract |

Alternative, directed method for producing the variant ApPDC-E469G-I468G by means of QuikChange®

Another method for producing the enzyme variant ApPDC-E469G/I468G would be, for example, the QuikChange® PCR method (U.S. Pat. Nos. 5,789,166, 5,932,419, 6,391,548). In this variant of the PCR a primer pair is used which carries the corresponding sequence modification instead of the DNA triplet code to be replaced. To produce the enzyme variant ApPDC-E469G/I468G the gene which encodes the variant ApPDC-E469G can be used. This so-called DNA template should be present cloned in a vector (for example pET22a). Instead of the triplet code which in position 1468 encodes the amino acid tryptophan, a primer which carries the glycine-encoding mutation at this position must be used (that is to say: GGA, GGT, GGC or GGG). All the further parameters of this QuikChange® PCR method and the selection of the primers required can be implemented by means of the instructions of the QuikChange® Site-Directed Mutagenesis Kit analogously to the manufacturers information (Agilent Technologies, Inc.) information.

DNA template (ApPDC-E469G) of the QuikChanqe® PCR method for producing the variant ApPDC-E469G-I468G (SEQ ID NO: 8)

ATGACCTATACTGTTGGCATGTATCTTGCAGAACGCCTTGTACAGATCGG

GCTGAAGCATCACTTCGCCGTGGCGGGCGACTACAATCTCGTTCTTCTGG

ATCAGTTGCTCCTCAACAAGGACATGAAACAGATCTATTGCTGCAATGAG

TTGAACTGTGGCTTCAGCGCGGAAGGCTACGCCCGTTCTAACGGGGCTGC

GGCAGCGGTTGTCACCTTCAGCGTTGGCGCCATTTCCGCCATGAACGCCC

TCGGCGGCGCCTATGCCGAAAACCTGCCGGTTATCCTGATTTCCGGCGCG

CCCAACAGCAATGATCAGGGCACAGGTCATATCCTGCATCACACAATCGG

CAAGACGGATTACAGCTACCAGCTTGAAATGGCCCGTCAGGTCACCTGTG

CCGCCGAAAGCATTACCGACGCTCACTCCGCCCCGGCCAAGATTGACCAC

GTCATTCGCACGGCGCTGCGCGAGCGTAAGCCGGCCTATCTGGACATCGC

GTGCAACATTGCCTCCGAGCCCTGCGTGCGGCCTGGCCCTGTCAGCAGCC

TGCTGTCCGAGCCTGAAATCGACCACACGAGCCTGAAGGCCGCAGTGGAC

GCCACGGTTGCCTTGCTGGAAAAATCGGCCAGCCCCGTCATGCTGCTGGG

CAGCAAGCTGCGGGCCGCCAACGCACTGGCCGCAACCGAAACGCTGGCAG

ACAAGCTGCAATGCGCGGTGACCATCATGGCGGCCGCGAAAGGCTTTT

TCCCCGA

-continued
```
AGACCACGCGGGTTTCCGCGGCCTGTACTGGGGCGAAGTCTCGAACCCCG

GCGTGCAGGAACTGGTGGAGACCTCCGACGCACTGCTGTGCATCGCCCCC

GTATTCAACGACTATTCAACAGTCGGCTGGTCGGCATGCCCAAGGGCCC

CAATGTGATTCTGGCTGAGCCCGACCGCGTAACGGTCGATGGCCGCGCCT

ATGACGGCTTTACCCTGCGCGCCTTCCTGCAGGCTCTGGCGGAAAAAGCC

CCCGCGCGCCCGGCCTCCGCACAGAAAAGCAGCGTCCCGACGTGCTCGCT

CACCGCGACATCCGATGAAGCCGGTCTGACGAATGACGAAATCGTCCGTC

ATATCAACGCCCTGCTGACATCAAACACGACGCTGGTGGCAGAAACCGGC

GATTCATGGTTCAATGCCATGCGCATGACCCTGCCGCGCGGTGCGCGCGT

GGAACTGGAAATGCAGTGGGGCCATATCGGCTGGTCCGTGCCCTCCGCCT

TCGGCAATGCCATGGGCTCGCAGGACCGCCAGCATGTGGTGATGGTAGGC

GATGGCTCCTTCCAGCTTACCGCGCAGGAAGTGGCTCAGATGGTGCGCTA

CGAACTGCCCGTCATTATCTTTCTGATCAACAACCGTGGCTATGTCATTG

GCATCGCCATTCATGACGGCCCGTACAACTATATCAAGAACTGGGATTAC

GCCGGCCTGATGGAAGTCTTCAACGCCGGAGAAGGCCATGGACTTGGCCT

GAAAGCCACCACCCCGAAGGAACTGACAGAAGCCATCGCCAGGGCAAAAG

CCAATACCCGCGGCCCGACGCTGATCGAATGCCAGATCGACCGCACGGAC

TGCACGGATATGCTGGTTCAATGGGGCCGCAAGGTTGCCTCAACCAACGC

GCGCAAGACCACTCTGGCCCTCGAG
```

In the sequence protocol, the sequence is shown with seq. no. 8. SEQ ID NO: 8 is disclosed here by way of example for a DNA which encodes the protein ApPDC-E469G to be modified, according to SEQ ID NO: 53. According to certain embodiments of the invention, however, all the other deoxyribonucleic acids which encode the starting protein to be modified can be employed for producing the enzyme to be modified. The nucleotides encoding these are known to a person skilled in the art.

Production of the Variants in the Form of "Whole Cells"

For expression of the enzymes in whole cells on a 1 l scale, cells from the master plate to which glycerol had been added were first transferred with an inoculation loop into 50 ml of LB medium (+100 μg/ml of ampicillin) and the mixture was incubated at 120 rpm and 37° C. in a 250 ml conical flask. After incubation for 16 h, 10 ml of the culture were added to 1 l of autoinduction medium and the mixture was incubated at 90 rpm and 20° C. in a 5 l conical flask for 72 h. The cells were then harvested by centrifugation (4° C., 6,000 rpm, 30 min) and stored at −20° C. until used further.

Autoinduction Medium

| | |
|---|---|
| 12 g/l | peptone |
| 24 g/l | yeast extract |
| 90 mM | potassium phosphate buffer (pH 7.5) |
| 0.5 g/l | glucose |
| 2 g/l | lactose |
| 0.01 g/l | ampicillin |
| 6.3 g/l | glycerol |

Production of the Variants in the Form of Cell Extracts 10 g of the cells cultured on a 1 l scale (see "Production of the variants in the form of whole cells") were resuspended on ice with 25 ml of breakdown buffer (50 mM potassium phosphate pH 6.5, 100 μM thiamine diphosphate, 2 mM magnesium sulfate), which was cooled to 4° C. The resuspended cells were then broken down by means of ultrasound (SD14 Sonotrode (Hielscher Ultrasonics GmbH), 4×2 min ultrasound treatment with cooling from ice for 1 min each time). To separate off the cell debris the solution was centrifuged (45 min, 18,000 rpm, 4° C.) and the supernatant (cell extract) was transferred into a new vessel.

Production of the Variants in the Form of Isolated Enzymes

For purification of the ApPDC variant by means of immobilized metal ion affinity chromatography and size exclusion chromatography, an ÄKTA™ purifier from Amersham Bioscience was used in order to detect inter alia the protein UV absorption (280 nm) and the electrical conductivity and to adjust the flow rate. For purification, 25 ml of the cell extract produced (see "Production of the variants in the form of cell extracts") was applied with a flow rate of 3 ml/min on to a column with a volume of 60 ml of Ni-NTA-Superflow (Qiagen N.V.), which was equilibrated beforehand with 180 ml of the application buffer. Thereafter, the column was flushed further with application buffer in a flow rate of 5 ml/min in order to remove proteins which do not bind or bind very weakly to the column material. After the UV absorption (280 nm) had reached a stable base line again, a wash buffer (50 mM potassium phosphate pH 6.5, 100 μM thiamine diphosphate, 2 mM magnesium sulfate, 50 mM imidazole) was used with a flow rate of 5 ml/min for elution of proteins which bind weakly to the column material. After a renewed stable UV absorption (280 nm), an elution buffer (50 mM potassium phosphate pH 6.5, 100 μM thiamine diphosphate, 2 mM magnesium sulfate, 250 mM imidazole) was used with a flow rate of 5 ml/min for elution of the target protein.

The eluate of the IMAC was applied for rebuffering with a flow rate of 10 ml/min to a size exclusion chromatography column (1 l column volume, Sephadex-G25, GE-Healthcare), which was flushed beforehand with 2 l of rebuffering buffer (10 mM potassium phosphate pH 6.5, 100 μM thiamine diphosphate, 2 mM magnesium sulfate). The fractions with increased UV absorption (280 nm) were combined and frozen in a crystallizing dish (−20° C.). For freeze drying, a reduced pressure of 0.22 mbar was applied to the frozen protein solution for 3 days.

In a further embodiment of the invention in the enzyme according to the invention, in addition to the replacement according to the invention in position no. 468, the amino acid tryptophan in position no. 543 is replaced by an amino acid which occupies less space than tryptophan.

These lyases additionally also have a positive influence on the increase in the stereoselectivity in the production of (S)-phenylacetylcarbinol.

With this preferred embodiment of the invention, an enantiomeric excess of 98% ee can be achieved.

The following lyases which meet this requirement may be mentioned as preferred:

ApPDC-E469G-I468G-W543H according to SEQ ID NO: 9 with histidine in position no. 543.

ApPDC-E469G-I468G-W543F according to SEQ ID NO: 10 with phenylalanine in position no. 543.

ApPDC-E469G-I468G-W543P according to SEQ ID NO: 11 with proline in position no. 543.

ApPDC-E469G-I468G-W543I according to SEQ ID NO: 12 with isoleucine in position no. 543.

ApPDC-E469G-I468G-W543L according to SEQ ID NO: 13 with leucine in position no. 543.

ApPDC-E469G-I468G-W543L according to SEQ ID NO: 14 with methionine in position no. 543.

ApPDC-E469G-I468G-W543V according to SEQ ID NO: 15 with valine in position no. 543.
ApPDC-E469G-I468G-W543A according to SEQ ID NO: 16 with alanine in position no. 543.
ApPDC-E469G-I468G-W543Y according to SEQ ID NO: 17 with tyrosine in position no. 543.
ApPDC-E469G-I468G-W543T according to SEQ ID NO: 18 with threonine in position no. 543.
ApPDC-E469G-I468G-W543G according to SEQ ID NO: 19 with glycine in position no. 543.
ApPDC-E469G-I468G-W543S according to SEQ ID NO: 20 with serine in position no. 543.
ApPDC-E469G-I468G-W543C according to SEQ ID NO: 21 with cysteine in position no. 543.
and
ApPDC-E469G-I468A-W543H according to SEQ ID NO: 22 with histidine in position no. 543.
ApPDC-E469G-I468A-W543F according to SEQ ID NO: 23 with phenylalanine in position no. 543.
ApPDC-E469G-I468A-W543P according to SEQ ID NO: 24 with proline in position no. 543.
ApPDC-E469G-I468A-W543I according to SEQ ID NO: 25 with isoleucine in position no. 543.
ApPDC-E469G-I468A-W543L according to SEQ ID NO: 26 with leucine in position no. 543.
ApPDC-E469G-I468A-W543M according to SEQ ID NO: 27 with methionine in position no. 543.
ApPDC-E469G-I468G-W543V according to SEQ ID NO: 28 with valine in position 543.
ApPDC-E469G-I468A-W543A according to SEQ ID NO: 29 with alanine in position no. 543.
ApPDC-E469G-I468A-W543Y according to SEQ ID NO: 30 with tyrosine in position no. 543.
ApPDC-E469G-I468A-W543T according to SEQ ID NO: 31 with threonine in position no. 543.
ApPDC-E469G-I468A-W543G according to SEQ ID NO: 32 with glycine in position no. 543.
ApPDC-E469G-I468A-W543S according to SEQ ID NO: 33 with serine in position no. 543.
ApPDC-E469G-I468A-W543C according to SEQ ID NO: 34 with cysteine in position no. 543.
and
ApPDC-E469G-I468V-W543H according to SEQ ID NO: 35 with histidine in position no. 543.
ApPDC-E469G-I468V-W543F according to SEQ ID NO: 36 with phenylalanine in position no. 543.
ApPDC-E469G-I468V-W543P according to SEQ ID NO: 37 with proline in position no. 543.
ApPDC-E469G-I468V-W543I according to SEQ ID NO: 38 with isoleucine in position no. 543.
ApPDC-E469G-I468V-W543L according to SEQ ID NO: 39 with leucine in position no. 543.
ApPDC-E469G-I468V-W543M according to SEQ ID NO: 40 with methionine in position no. 543.
ApPDC-E469G-I468V-W543V according to SEQ ID NO: 41 with valine in position no. 543.
ApPDC-E469G-I468V-W543A according to SEQ ID NO: 42 with alanine in position no. 543.
ApPDC-E469G-I468V-W543Y according to SEQ ID NO: 43 with tyrosine in position no. 543.
ApPDC-E469G-I468V-W543T according to SEQ ID NO: 44 with threonine in position no. 543.
ApPDC-E469G-I468V-W543G according to SEQ ID NO: 45 with glycine in position no. 543.
ApPDC-E469G-I468V-W543S according to SEQ ID NO: 46 with serine in position no. 543.
ApPDC-E469G-I468V-W543C according to SEQ ID NO: 47 with cysteine in position no. 543.

Deoxyribonucleic acids which encode the enzymes mentioned are furthermore provided according to certain embodiments of the invention.

According to certain embodiments of the invention, these are deoxyribonucleic acids which encode a variant of the enzyme ApPDC-E469G and which in position no. 1402-1404 encode an amino acid which occupies a reduced space with respect to isoleucine, and which in position no. 1627-1629 additionally encode an amino acid which occupies less space than tryptophan.

For the example of the protein according to SEQ ID NO: 23, the nucleic acids GCC, for example, can be in positions no. 1402-1404 of the corresponding deoxyribonucleic acid and the nucleic acids TTT can be in positions no. 1627-1629. The corresponding nucleotide sequence is listed in the sequence protocol under number 48.

A DNA encoding the enzymes according to the invention according to sequences 9 to 47 can be produced by directed or non-directed mutagenesis by methods known to a person skilled in the art. Directed mutagenesis is preferred in this context. These methods are known to a person skilled in the art. An example of producing an embodiment of the invention is disclosed concretely in the specific description part. This procedure can also be employed in principle for all the other deoxyribonucleic acids and enzymes disclosed, so that all the enzymes and deoxyribonucleic acids according to the invention can be produced by an analogous route.

The deoxyribonucleic acids can be ligated into a vector, preferably a plasmid.

Empty vectors which can be employed are, for example, pET-20b(+), pET-21a-d(+), pET-22b(+), pET-23a-d(+), pET-24a-d(+), pET-25b(+), pET-26b(+), pET-27b(+), pET-28a(+), pET-29a-c(+), pET-30a-c(+), pET-31b(+), pET-34b(+), pET-35b(+), pET-36b(+), pET-37b(+), pET-38b(+), into which the corresponding DNA according to the invention is ligated.

Alternatively, the deoxyribonucleic acids can also be ligated into the genome.

The ligated deoxyribonucleic acids are DNAs which encode a variant of the enzyme ApPDC-E469G and which in position no. 1402-1404 encode an amino acid which occupies a reduced space with respect to isoleucine, and which in position no. 1627-1629 encode an amino acid which occupies a reduced space with respect to tryptophan.

Preferably, the ligated deoxyribonucleic acid encodes the proteins according to SEQ ID NOs: 9 to 47.

According to the invention, vectors can be provided which contain a deoxyribonucleic acid which encodes a variant of the enzyme ApPDC-E469G and which in position 1402-1404 encodes an amino acid which occupies a reduced space with respect to isoleucine, and which in position no. 1627-1629 additionally encodes an amino acid which occupies a reduced space with respect to tryptophan.

Preferably, the vector contains a deoxyribonucleic acid according to SEQ ID NO: 48.

Preferably, the vector is a plasmid.

SEQ ID NO: 49 shows by way of example a sequence for a plasmid according to the invention which contains a DNA according to SEQ ID NO: 48.

According to the invention, in an embodiment of the invention benzaldehyde is also reacted with pyruvate or with acetaldehyde according to formula (1) by means of a variant of the enzyme ApPDC-E469G, which has in position no. 468 an amino acid which occupies a reduced space with respect to isoleucine and which has in position no. 543 an amino acid which occupies a reduced space with respect to tryptophan, preferably an enzyme from the group according to SEQ ID NO: 9 to 47, to give (S)-phenylacetylcarbinol.

Formula (1)

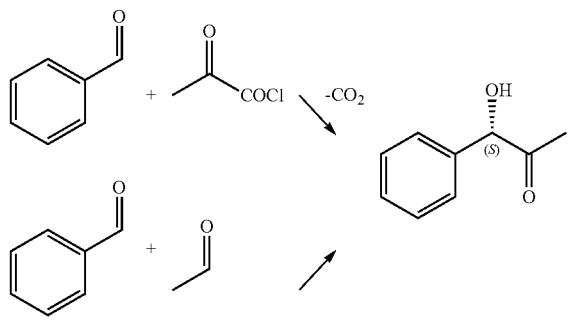

The reaction is preferably carried out in aqueous solution.

The pH is in a range of 5-9, preferably 6.5-8, particularly preferably 6.5-7.

In this reaction, potassium phosphate buffer, HEPES, MOPS, TEA or TRIS-HCl, for example, can be employed as a buffer.

Thiamine diphosphate and magnesium sulfate can furthermore be employed as cofactors.

The reaction can be carried out in vivo or in vitro.

For the in vivo production of (S)-phenylacetylcarbinol, for example, *E. coli*, a *Corynebacterium*, for example *Corynebacterium glutamicum*, or a yeast, such as *Saccharomyces cerevisiae*, can be employed as the production organism.

For this, the production organisms are transformed with the DNA according to an embodiment of the invention or a vector which contains the DNA.

The DNA can also be introduced into the genome in the production organism.

The genes employed are expressed heterologously in this context.

For the in vitro production either the isolated enzyme or the cell extract of the production organism can be employed.

Typical temperatures are between 20° C. and 40° C., 20° C. to 30° C. are preferred and a temperature of from 20° C. to 25° C. is particularly preferred.

The reaction times can be 2 h-48 h, preferably 6 h-24 h, particularly preferably 12 h.

Some examples, which are not to be interpreted as limiting, are described in the following.

The reactions can be carried out in a conventional set-up in a reaction flask with stirring.

In order to be able to produce (S)-PAC in high enantiomeric excesses, a variant of the enzyme ApPDC-E469G was produced by mutagenesis. The variant ApPDC-E469G-I468A-W543F produces (S)-PAC using isolated enzymes with an ee of 98%. Using ApPDC-E469G-I468A-W543F, which was expressed heterologously in *Escherichia coli* and is employed as an inexpensive whole cell catalyst, (S)-PAC with an ee of 96% can be generated.

Example 3

20 mM benzaldehyde, 400 mM pyruvate, 2.5 mM magnesium sulfate, 100 µM thiamine diphosphate, 20 mg/ml (moist weight) ApPDC-E469G-I468A-W543F (whole cells of *E. coli* in which ApPDC-E469G-I468A-W543F was expressed), 50 mM potassium phosphate buffer pH 6.5, 25° C., reaction time: 48 h.

Enantiomeric purity of (S)-PAC: ee 96%
Yield: 73%.

Example 4

20 mM benzaldehyde, 400 mM pyruvate, 2.5 mM magnesium sulfate, 100 µM thiamine diphosphate, 1 mg/ml ApPDC-E469G-I468A-W543F, 20 mM benzaldehyde, 400 mM pyruvate, 2.5 mM magnesium sulfate, 100 µM thiamine diphosphate, 1 mg/ml ApPDC-E469G-I468G (isolated enzyme), 50 mM potassium phosphate buffer pH 6.5, 25° C., reaction time: 48 h, 50 mM potassium phosphate buffer pH 6.5, 25° C., reaction time: 48 h.

Enantiomeric purity of (S)-PAC: ee 98%
Yield: 45%.

Directed Method for Producing the Variant ApPDC-E469G-I468A-W543F by Means of QuikChange® Starting from ApPDC-E469G-I468A-W543

For producing the enzyme variant ApPDC-E469G-I468A-W543F, the QuikChange® PCR method (U.S. Pat. Nos. 5,789,166, 5,932,419, 6,391,548) was used. In this variant of the PCR, a primer pair is used which carries the corresponding sequence modification instead of the DNA triplet code to be replaced. To produce the enzyme variant ApPDC-E469G-I468A-W543F, the gene which encodes the variant ApPDC-E469G-I468A-W543 was used. This DNA template was present cloned in a vector (for example pET22a). Instead of the triplet code which in position W543 encodes the amino acid tryptophan, a primer which carries the phenylalanine-encoding mutation at this position must be used (that is to say, for example, TTC or TTT).

Primers of the QuikChange® PCR method for producing the enzyme variant ApPDC-E469G-I468A-W543F starting from ApPDC-E469G-I468A-W543

```
forward:
                                      (seq. no. 50)
5' ACCTTGCGGCCGAATTGAACCAGCATATCCGTGC 3' reverse:
                                      (seq. no. 51)
5' GCACGGATATGCTGGTTCAATTCGGCCGCAAGGT 3'
```

A master solution was first prepared and then divided into four batches of 50 µl each. To start the reaction 1 µl of PfuTurbo® DNA Polymerase was added.

PCR Reaction Batch:
1 portion of PCR buffer
0.2 mM nucleotides
0.25 pmol of forward primer
0.25 pmol of reverse primer
0.1 ng/µl of DNA template The reaction was carried out under the following conditions:

| | Duration (min) | Temperature (° C.) | Repetitions |
|---|---|---|---|
| Initialization | 2:00 | 95 | |
| Denaturing | 2:00 | 95 | |
| Annealing | 1:00 | 79° C. | 20x |
| Elongation | 6:00 | 70 | |
| Termination | 10:00 | 70 | |

To digest the template DNA, 1 µl of the enzyme DpnI (Eppendorf) was added to the solution and the batch was incubated at 37° C. for 1 h. The entire batch was then purified with the DNA Purification Kit (list of chemicals) before the further transformation.

All the further parameters of this QuikChange® PCR method and the selection of the primers required for further enzyme variants can be implemented by means of the instructions of the QuikChange® Site-Directed Mutagenesis Kit analogously to the manufacturer's information (Agilent Technologies, Inc.) information.

DNA template (ApPDC-E469G-I468A) of the QuikChanqe® PCR method for producing the variant ApPDC-E469G-I468A-W543F (SEQ ID NO: 52)

ATGACCTATACTGTTGGCATGTATCTTGCAGAACGCCTTGTACAGATCGG

GCTGAAGCATCACTTCGCCGTGGCGGGCGACTACAATCTCGTTCTTCTGG

ATCAGTTGCTCCTCAACAAGGACATGAAACAGATCTATTGCTGCAATGAG

TTGAACTGTGGCTTCAGCGCGGAAGGCTACGCCCGTTCTAACGGGCTGC

GGCAGCGGTTGTCACCTTCAGCGTTGGCGCCATTTCCGCCATGAACGCCC

TCGGCGGCGCCTATGCCGAAAACCTGCCGGTTATCCTGATTTCCGGCGCG

CCCAACAGCAATGATCAGGGCACAGGTCATATCCTGCATCACACAATCGG

CAAGACGGATTACAGCTACCAGCTTGAAATGGCCCGTCAGGTCACCTGTG

CCGCCGAAAGCATTACCGACGCTCACTCCGCCCGGCCAAGATTGACCAC

GTCATTCGCACGGCGCTGCGCGAGCGTAAGCCGGCCTATCTGGACATCGC

GTGCAACATTGCCTCCGAGCCCTGCGTGCGGCCTGGCCCTGTCAGCAGCC

TGCTGTCCGAGCCTGAAATCGACCACACGAGCCTGAAGGCCGCAGTGGAC

GCCACGGTTGCCTTGCTGGAAAAATCGGCCAGCCCCGTCATGCTGCTGGG

CAGCAAGCTGCGGGCCGCCAACGCACTGGCCGCAACCGAAACGCTGGCAG

ACAAGCTGCAATGCGCGGTGACCATCATGGCGGCCGCGAAAGGCTTTTTC

CCCGAAGACCACGCGGGTTCCGCGGCCTGTACTGGGGCGAAGTCTCGAA

CCCCGGCGTGCAGGAACTGGTGGAGACCTCCGACGCACTGCTGTGCATCG

CCCCCGTATTCAACGACTATTCAACAGTCGGCTGGTCGGCATGGCCCAAG

GGCCCCAATGTGATTCTGGCTGAGCCCGACCGCGTAACGGTCGATGGCCG

CGCCTATGACGGCTTTACCCTGCGCGCCTTCCTGCAGGCTCTGGCGGAAA

AAGCCCCCGCGCCCGGCCTCCGCACAGAAAAGCAGCGTCCCGACGTGC

TCGCTCACCGCGACATCCGATGAAGCCGGTCTGACGAATGACGAAATCGT

CCGTCATATCAACGCCCTGCTGACATCAAACACGACGCTGGTGGCAGAAA

CCGGCGATTCATGGTTCAATGCCATGCGCATGACCCTGCCGCGCGGTGCG

CGCGTGGAACTGGAAATGCAGTGGGGCCATATCGGCTGGTCCGTGCCCTC

CGCCTTCGGCAATGCCATGGGCTCGCAGGACCGCCAGCATGTGGTGATGG

TAGGCGATGGCTCCTTCCAGCTTACCGCGCAGGAAGTGGCTCAGATGGTG

CGCTACGAACTGCCCGTCATTATCTTTCTGATCAACAACCGTGGCTATGT

CGCCGGCATCGCCATTCATGACGGCCCGTACAACTATATCAAGAACTGGG

ATTACGCCGGCCTGATGGAAGTCTTCAACGCCGGAGAAGGCCATGGACTT

GGCCTGAAAGCCACCACCCCGAAGGAACTGACAGAAGCCATCGCCAGGGC

AAAAGCCAATACCCGCGGCCCGACGCTGATCGAATGCCAGATCGACCGCA

CGGACTGCACGGATATGCTGGTTCAATGGGGCCGCAAGGTTGCCTCAACC

AACGCGCGCAAGACCACTCTGGCCCTCGAG

SEQ ID NO: 52 is disclosed here by way of example for a DNA which encodes the protein ApPDC-E469G-I468A to be modified, according to SEQ ID NO: 2. According to certain embodiments of the invention, however, all the other deoxyribonucleic acids which encode the starting protein to be modified can be employed for producing the enzyme to be modified. The nucleotides encoding these are known to a person skilled in the art.

Transformation of *E. coli* BL21-DE3 and *E. coli* DH5α

The strains *E. coli* BL21-DE3 and *E. coli* DH5α were transformed with the DNA produced by site saturation mutagenesis. For this, 100 ng of the DNA were added to 50 µl of competent cells and the batch was incubated on ice for 30 min. A heat shock was then carried out at 42° C. for 90 sec. After 3 min on ice, 500 µl of SOC medium were added and the solution was then incubated in an Eppendorf Thermomixer at 350 rpm and 37° C. for 45 min. After the incubation had been carried out, the cell suspension was centrifuged at 13,000 rpm in an Eppendorf bench centrifuge for 30 sec and the pellet was then resuspended in 100 µl of supernatant. The cell suspension, which had been concentrated to 100 µl, was plated out on LB agar plates (with 100 µg/ml of ampicillin) and incubated upside-down at 37° C. for 16 h.

DNA Isolation and Identification of the Best Enzyme Variants by DNA Sequencing

The DNA of the enzyme which gave the highest ee values for (S)-PAC in the carboligation reactions was sequenced starting from the master plate for identification of the mutation. For this cells were first transferred with an inoculation loop from the master plate to which glycerol had been added into 50 ml of LB medium (+50 µg/ml of ampicillin) and the mixture was incubated at 37° C. in a 250 ml conical flask. After incubation for 12 h, 20 ml of the cell suspension were centrifuged (4,000 rpm, 5 min, 4° C.). The DNA of the cells in the pellet was isolated by the method of the QIAprep® Spin Miniprep Kit analogously to the manufacturers instructions (Qiagen N.V.). In addition the concentration of the DNA was adjusted to 100 ng/µl and the DNA was sequenced by LGC Genomics GmbH.

LB (Lysogeny Broth) Medium

| | |
|---|---|
| 10 g/l | NaCl |
| 10 g/l | peptone |
| 5 g/l | yeast extract |

Production of the Variants in the Form of "Whole Cells"

For expression of the enzymes in whole cells on a 1 l scale, cells from the master plate to which glycerol had been added were first transferred with an inoculation loop into 50 ml of LB medium (+100 µg/ml of ampicillin) and the mixture was incubated at 120 rpm and 37° C. in a 250 ml conical flask. After incubation for 16 h, 10 ml of the culture were added to 1 l of autoinduction medium and the mixture was incubated at 90 rpm and 20° C. in a 5 l conical flask for 72 h. The cells were then harvested by centrifugation (4° C., 6,000 rpm, 30 min) and stored at −20° C. until used further.

Autoinduction Medium

| | |
|---|---|
| 12 g/l | peptone |
| 24 g/l | yeast extract |
| 90 mM | potassium phosphate buffer (pH 7.5) |
| 0.5 g/l | glucose |
| 2 g/l | lactose |
| 0.01 g/l | ampicillin |
| 6.3 g/l | glycerol |

Production of the Variants in the Form of Isolated Enzymes 10 g of the cells cultured on a 1 l scale were resuspended on ice with 25 ml of breakdown buffer (50 mM potassium phosphate pH 6.5, 100 µM thiamine diphosphate, 2 mM magnesium sulfate), which was cooled to 4° C. The resuspended cells were then broken down by means of ultrasound (SD14 Sonotrode (Hielscher Ultrasonics GmbH), 4×2 min ultrasound treatment with cooling from ice for 1 min each time). To separate off the cell debris the solution was centrifuged (45 min, 18,000 rpm, 4° C.) and the supernatant (cell extract) was transferred into a new vessel.

For purification of the ApPDC variant by means of immobilized metal ion affinity chromatography and size exclusion chromatography, an ÄKTA™ purifier from Amersham Bioscience was used in order to detect inter alia the protein UV absorption (280 nm) and the electrical conductivity and to adjust the flow rate. For purification, the cell extract produced 25 ml) was applied with a flow rate of 3 ml/min on to a column with a volume of 60 ml of Ni-NTA-Superflow (Qiagen N.V.), which was equilibrated beforehand with 180 ml of the application buffer. Thereafter, the column was flushed further with application buffer in a flow rate of 5 ml/min in order to remove proteins which are not bound or bind very weakly to the column material. After the UV absorption (280 nm) had reached a stable base line again, a wash buffer (50 mM potassium phosphate pH 6.5, 100 µM thiamine diphosphate, 2 mM magnesium sulfate, 50 mM imidazole) was used with a flow rate of 5 ml/min for elution of proteins which bind weakly to the column material. After a renewed stable UV absorption (280 nm), an elution buffer (50 mM potassium phosphate pH 6.5, 100 µM thiamine diphosphate, 2 mM magnesium sulfate, 250 mM imidazole) was used with a flow rate of 5 ml/min for elution of the target protein.

The eluate of the IMAC was applied for rebuffering with a flow rate of 10 ml/min to a size exclusion chromatography column (1 l column volume, Sephadex-G25, GE-Healthcare), which was flushed beforehand with 2 l of rebuffering buffer (10 mM potassium phosphate pH 6.5, 100 µM thiamine diphosphate, 2 mM magnesium sulfate). The fractions with increased UV absorption (280 nm) were combined and frozen in a crystallizing dish (−20° C.). For freeze drying, a reduced pressure of 0.22 mbar was applied to the frozen protein solution for 3 days. The powder formed had a protein content of 20%. The purity (content of the target protein with respect to foreign proteins) was >90%.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A lyase comprising the amino acid sequence of SEQ ID NO: 1, 2, 3, 10, or 23.

2. A deoxyribonucleic acid (DNA) molecule encoding the lyase of claim 1.

3. A vector comprising the DNA molecule of claim 2.

4. The vector of claim 3, wherein the vector is a plasmid.

5. The vector of claim 4, wherein the DNA molecule is ligated into an empty vector selected from the group consisting of pET-20b(+), pET-21a-d(+), pET-22b(+), pET-23a-d(+), pET-24a-d(+), pET-25b(+), pET-26b(+), pET-27b(+), pET-28a(+), pET-29a-c(+), pET-30a-c(+), pET31b(+), pET-34b(+), pET-35b(+), pET-36b(+), pET-37b(+), and pET-38b (+).

6. A method for producing (S)-phenylacetylcarbinol, comprising reacting the lyase of claim 1 with benzaldehyde and either pyruvate or acetaldehyde to produce (S)-phenylacetylcarbinol.

7. The method of claim 6, wherein the reaction is carried out at a pH of 5-9.

8. The method of claim 6, wherein HEPES, MOPS, TEA or TRIS-HCl is employed as a buffer for the reaction.

9. The method of claim 6, wherein thiamine phosphate and magnesium sulfate are employed as cofactors in the reaction.

10. The method of claim 6, wherein the reaction is carried out in a microorganism.

11. The method of claim 10, wherein the microorganism is selected from the group consisting of an *E. coli*, a *Corynebacterium*, and a yeast.

12. The method of claim 11, wherein the microorganism is transformed with at least one DNA molecule comprising the nucleotide sequence of SEQ ID NO: 4, 48, or 52.

13. The method of claim 12, wherein a vector comprising the at least one DNA molecule comprising the nucleotide sequence of SEQ ID NO: 4, 48, or 52 is employed for the transformation.

14. The method of claim 6, wherein the reaction is carried out in vitro.

15. The method of claim 14, wherein the reaction is carried out in a crude cell extract from a microorganism that produces the lyase.

16. The DNA molecule of claim 2, wherein the DNA molecule comprises the nucleotide sequence of SEQ ID NO: 4, 48, or 52.

17. The vector of claim 3, wherein the DNA molecule comprises the nucleotide sequence of SEQ ID NO: 4, 48, or 52.

18. The method of claim 12, wherein the at least one DNA molecule comprising the nucleotide sequence of SEQ ID NO: 4, 48, or 52 is integrated into the genome of the microorganism.

19. The lyase of claim 1, wherein the lyase comprises the amino acid sequence of SEQ ID NO: 1 or 2.

20. The lyase of claim 1, wherein the lyase comprises the amino acid sequence of SEQ ID NO: 23.

* * * * *

SEQUENCE LISTING

```
<160> NUMBER OF SEQ ID NOS: 53

<210> SEQ ID NO 1
<211> LENGTH: 560
<212> TYPE: PRT
<213> ORGANISM: Artificial Sequence
<220> FEATURE:
<223> OTHER INFORMATION: Synthetic

<400> SEQUENCE: 1

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
```

-continued

```
                 50                  55                  60
Gly Ala Ala Ala Val Val Thr Phe Ser Val Gly Ala Ile Ser Ala
 65                  70                  75                  80
Met Asn Ala Leu Gly Gly Ala Tyr Ala Glu Asn Leu Pro Val Ile Leu
                 85                  90                  95
Ile Ser Gly Ala Pro Asn Ser Asn Asp Gln Gly Thr Gly His Ile Leu
                100                 105                 110
His His Thr Ile Gly Lys Thr Asp Tyr Ser Tyr Gln Leu Glu Met Ala
            115                 120                 125
Arg Gln Val Thr Cys Ala Ala Glu Ser Ile Thr Asp Ala His Ser Ala
            130                 135                 140
Pro Ala Lys Ile Asp His Val Ile Arg Thr Ala Leu Arg Glu Arg Lys
145                 150                 155                 160
Pro Ala Tyr Leu Asp Ile Ala Cys Asn Ile Ala Ser Glu Pro Cys Val
                165                 170                 175
Arg Pro Gly Pro Val Ser Ser Leu Leu Ser Glu Pro Glu Ile Asp His
                180                 185                 190
Thr Ser Leu Lys Ala Ala Val Asp Ala Thr Val Ala Leu Leu Glu Lys
            195                 200                 205
Ser Ala Ser Pro Val Met Leu Leu Gly Ser Lys Leu Arg Ala Ala Asn
210                 215                 220
Ala Leu Ala Ala Thr Glu Thr Leu Ala Asp Lys Leu Gln Cys Ala Val
225                 230                 235                 240
Thr Ile Met Ala Ala Lys Gly Phe Phe Pro Glu Asp His Ala Gly
                245                 250                 255
Phe Arg Gly Leu Tyr Trp Gly Glu Val Ser Asn Pro Gly Val Gln Glu
                260                 265                 270
Leu Val Glu Thr Ser Asp Ala Leu Leu Cys Ile Ala Pro Val Phe Asn
            275                 280                 285
Asp Tyr Ser Thr Val Gly Trp Ser Ala Trp Pro Lys Gly Pro Asn Val
            290                 295                 300
Ile Leu Ala Glu Pro Asp Arg Val Thr Val Asp Gly Arg Ala Tyr Asp
305                 310                 315                 320
Gly Phe Thr Leu Arg Ala Phe Leu Gln Ala Leu Ala Glu Lys Ala Pro
                325                 330                 335
Ala Arg Pro Ala Ser Ala Gln Lys Ser Ser Val Pro Thr Cys Ser Leu
                340                 345                 350
Thr Ala Thr Ser Asp Glu Ala Gly Leu Thr Asn Asp Glu Ile Val Arg
            355                 360                 365
His Ile Asn Ala Leu Leu Thr Ser Asn Thr Thr Leu Val Ala Glu Thr
            370                 375                 380
Gly Asp Ser Trp Phe Asn Ala Met Arg Met Thr Leu Pro Arg Gly Ala
385                 390                 395                 400
Arg Val Glu Leu Glu Met Gln Trp Gly His Ile Gly Trp Ser Val Pro
                405                 410                 415
Ser Ala Phe Gly Asn Ala Met Gly Ser Gln Asp Arg Gln His Val Val
                420                 425                 430
Met Val Gly Asp Gly Ser Phe Gln Leu Thr Ala Gln Glu Val Ala Gln
            435                 440                 445
Met Val Arg Tyr Glu Leu Pro Val Ile Ile Phe Leu Ile Asn Asn Arg
            450                 455                 460
Gly Tyr Val Gly Gly Ile Ala Ile His Asp Gly Pro Tyr Asn Tyr Ile
465                 470                 475                 480
```

Lys Asn Trp Asp Tyr Ala Gly Leu Met Glu Val Phe Asn Ala Gly Glu
            485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Trp Gly
            530                 535                 540

Arg Lys Val Ala Ser Thr Asn Ala Arg Lys Thr Thr Leu Ala Leu Glu
545                 550                 555                 560

<210> SEQ ID NO 2
<211> LENGTH: 560
<212> TYPE: PRT
<213> ORGANISM: Artificial Sequence
<220> FEATURE:
<223> OTHER INFORMATION: Synthetic

<400> SEQUENCE: 2

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
        50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
            85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
            165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
            245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

```
Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
    450                 455                 460

Gly Tyr Val Ala Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Trp Gly
    530                 535                 540

Arg Lys Val Ala Ser Thr Asn Ala Arg Lys Thr Thr Leu Ala Leu Glu
545                 550                 555                 560
```

<210> SEQ ID NO 3
<211> LENGTH: 560
<212> TYPE: PRT
<213> ORGANISM: Artificial Sequence
<220> FEATURE:
<223> OTHER INFORMATION: Synthetic

<400> SEQUENCE: 3

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
        50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95
```

```
Ile Ser Gly Ala Pro Asn Ser Asn Asp Gln Gly Thr Gly His Ile Leu
            100                 105                 110
His His Thr Ile Gly Lys Thr Asp Tyr Ser Tyr Gln Leu Glu Met Ala
        115                 120                 125
Arg Gln Val Thr Cys Ala Ala Glu Ser Ile Thr Asp Ala His Ser Ala
    130                 135                 140
Pro Ala Lys Ile Asp His Val Ile Arg Thr Ala Leu Arg Glu Arg Lys
145                 150                 155                 160
Pro Ala Tyr Leu Asp Ile Ala Cys Asn Ile Ala Ser Glu Pro Cys Val
                165                 170                 175
Arg Pro Gly Pro Val Ser Ser Leu Leu Ser Glu Pro Glu Ile Asp His
            180                 185                 190
Thr Ser Leu Lys Ala Ala Val Asp Ala Thr Val Ala Leu Leu Glu Lys
        195                 200                 205
Ser Ala Ser Pro Val Met Leu Leu Gly Ser Lys Leu Arg Ala Ala Asn
    210                 215                 220
Ala Leu Ala Ala Thr Glu Thr Leu Ala Asp Lys Leu Gln Cys Ala Val
225                 230                 235                 240
Thr Ile Met Ala Ala Ala Lys Gly Phe Phe Pro Glu Asp His Ala Gly
                245                 250                 255
Phe Arg Gly Leu Tyr Trp Gly Glu Val Ser Asn Pro Gly Val Gln Glu
            260                 265                 270
Leu Val Glu Thr Ser Asp Ala Leu Leu Cys Ile Ala Pro Val Phe Asn
        275                 280                 285
Asp Tyr Ser Thr Val Gly Trp Ser Ala Trp Pro Lys Gly Pro Asn Val
    290                 295                 300
Ile Leu Ala Glu Pro Asp Arg Val Thr Val Asp Gly Arg Ala Tyr Asp
305                 310                 315                 320
Gly Phe Thr Leu Arg Ala Phe Leu Gln Ala Leu Ala Glu Lys Ala Pro
                325                 330                 335
Ala Arg Pro Ala Ser Ala Gln Lys Ser Ser Val Pro Thr Cys Ser Leu
            340                 345                 350
Thr Ala Thr Ser Asp Glu Ala Gly Leu Thr Asn Asp Glu Ile Val Arg
        355                 360                 365
His Ile Asn Ala Leu Leu Thr Ser Asn Thr Thr Leu Val Ala Glu Thr
    370                 375                 380
Gly Asp Ser Trp Phe Asn Ala Met Arg Met Thr Leu Pro Arg Gly Ala
385                 390                 395                 400
Arg Val Glu Leu Glu Met Gln Trp Gly His Ile Gly Trp Ser Val Pro
                405                 410                 415
Ser Ala Phe Gly Asn Ala Met Gly Ser Gln Asp Arg Gln His Val Val
            420                 425                 430
Met Val Gly Asp Gly Ser Phe Gln Leu Thr Ala Gln Glu Val Ala Gln
        435                 440                 445
Met Val Arg Tyr Glu Leu Pro Val Ile Ile Phe Leu Ile Asn Asn Arg
    450                 455                 460
Gly Tyr Val Val Gly Ile Ala Ile His Asp Gly Pro Tyr Asn Tyr Ile
465                 470                 475                 480
Lys Asn Trp Asp Tyr Ala Gly Leu Met Glu Val Phe Asn Ala Gly Glu
                485                 490                 495
Gly His Gly Leu Gly Leu Lys Ala Thr Thr Pro Lys Glu Leu Thr Glu
            500                 505                 510
```

| Ala | Ile | Ala | Arg | Ala | Lys | Ala | Asn | Thr | Arg | Gly | Pro | Thr | Leu | Ile | Glu |
|---|---|---|---|---|---|---|---|---|---|---|---|---|---|---|---|
| | | 515 | | | | 520 | | | | | 525 | | | | |

Cys Gln Ile Asp Arg Thr Asp Cys Thr Asp Met Leu Val Gln Trp Gly
530                     535                     540

Arg Lys Val Ala Ser Thr Asn Ala Arg Lys Thr Thr Leu Ala Leu Glu
545                 550                     555                     560

<210> SEQ ID NO 4
<211> LENGTH: 1680
<212> TYPE: DNA
<213> ORGANISM: Artificial Sequence
<220> FEATURE:
<223> OTHER INFORMATION: Synthetic

<400> SEQUENCE: 4

```
atgacctata ctgttggcat gtatcttgca gaacgccttg tacagatcgg gctgaagcat      60
cacttcgccg tggcgggcga ctacaatctc gttcttctgg atcagttgct cctcaacaag     120
gacatgaaac agatctattg ctgcaatgag ttgaactgtg gcttcagcgc ggaaggctac     180
gcccgttcta acggggctgc ggcagcggtt gtcaccttca gcgttggcgc catttccgcc     240
atgaacgccc tcggcggcgc ctatgccgaa aacctgccgg ttatcctgat tccggcgcg      300
cccaacagca atgatcaggg cacaggtcat atcctgcatc acacaatcgg caagacggat     360
tacagctacc agcttgaaat ggcccgtcag gtcacctgtg ccgccgaaag cattaccgac     420
gctcactccg ccccggccaa gattgaccac gtcattcgca cggcgctgcg cgagcgtaag     480
ccggcctatc tggacatcgc gtgcaacatt gcctccgagc cctgcgtgcg gcctggccct     540
gtcagcagcc tgctgtccga gcctgaaatc gaccacacga gctgaaggc cgcagtggac      600
gccacggttg ccttgctgga aaaatcggcc agccccgtca tgctgctggg cagcaagctg     660
cgggccgcca acgcactggc cgcaaccgaa cgctggcag acaagctgca atgcgcggtg      720
accatcatgg cggccgcgaa aggctttttc cccgaagacc acgcgggttt ccgcggcctg     780
tactggggcg aagtctcgaa ccccggcgtg caggaactgg tggagacctc cgacgcactg     840
ctgtgcatcg cccccgtatt caacgactat tcaacagtcg gctggtcggc atggcccaag     900
ggcccccaatg tgattctggc tgagcccgac cgcgtaacgg tcgatggccg cgcctatgac     960
ggctttaccc tgcgcgcctt cctgcaggct ctggcggaaa agccccccgc gcgcccggcc    1020
tccgcacaga aaagcagcgt cccgacgtgc tcgctcaccg cgacatccga tgaagccggt    1080
ctgacgaatg acgaaatcgt ccgtcatatc aacgccctgc tgacatcaaa cacgacgctg    1140
gtggcagaaa ccggcgattc atggttcaat gccatgcgca tgaccctgcc gcgcggtgcg    1200
cgcgtggaac tggaaatgca gtggggccat atcggctggt ccgtgccctc gccttcggc     1260
aatgccatgg gctcgcagga ccgccagcat gtggtgatgg taggcgatgg ctcccttccag    1320
cttaccgcgc aggaagtggc tcagatggtg cgctacgaac tgcccgtcat tatctttctg    1380
atcaacaacc gtggctatgt cggtggcatc gccattcatg acggcccgta caactatatc    1440
aagaactggg attacgccgg cctgatggaa gtcttcaacg ccggagaagg ccatggactt    1500
ggcctgaaag ccaccacccc gaaggaactg acagaagcca tcgccagggc aaaagccaat    1560
acccgcggcc cgacgctgat cgaatgccag atcgaccgca cggactgcac ggatatgctg    1620
gttcaatggg gccgcaaggt tgcctcaacc aacgcgcgca agaccactct ggccctcgag    1680
```

<210> SEQ ID NO 5
<211> LENGTH: 7041
<212> TYPE: DNA

<213> ORGANISM: Artificial Sequence
<220> FEATURE:
<223> OTHER INFORMATION: Synthetic

<400> SEQUENCE: 5

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taagggattt tgccgatttc ggcctattgg ttaaaaaatg agctgattta     420
acaaaaattt aacgcgaatt ttaacaaaat attaacgttt acaatttcag gtggcactt     480
tcggggaaat gtgcgcggaa cccctatttg tttatttttc taaatacatt caaatatgta     540
tccgctcatg agacaataac cctgataaat gcttcaataa tattgaaaaa ggaagagtat     600
gagtattcaa catttccgtg tcgcccttat ccctttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca acatggggg atcatgtaa ctcgccttga     1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca gtttactca tatatacttt agattgattt    1500
aaaacttcat ttttaattta aaaggatcta ggtgaagatc cttttttgata atctcatgac    1560
caaaatccct taacgtgagt tttcgttcca ctgagcgtca gaccccgtag aaaagatcaa    1620
aggatcttct tgagatcctt tttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacataccte gctctgctaa tcctgttacc    1860
agtggctgct gccagtggcg ataagtcgtg tcttaccggg ttggactcaa gacgatagtt    1920
accggataag gcgcagcggt cgggctgaac gggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcgaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
```

```
cgccagcaac gcggccttt tacggttcct ggccttttgc tggccttttg ctcacatgtt    2280
ctttcctgcg ttatcccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaagggg atttctgttc atggggtaa    2880
tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt ttggtggcgg    3360
gaccagtgac gaaggcttga gcagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcgcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa ataatactg    4260
ttgatgggtg tctggtcaga gacatcaaga ataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg caacgccaa tcagcaacga ctgtttgccc    4560
```

```
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccatacce acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
ctcgatcccg cgaaattaat acgactcact atagggaat tgtgagcgga taacaattcc    5160
cctctagaaa taattttgtt aactttaag aaggagatat acatatgacc tatactgttg    5220
gcatgtatct tgcagaacgc cttgtacaga tcgggctgaa gcatcacttc gccgtggcgg    5280
gcgactacaa tctcgttctt ctggatcagt tgctcctcaa caaggacatg aaacagatct    5340
attgctgcaa tgagttgaac tgtggcttca gcgcggaagg ctacgcccgt tctaacgggg    5400
ctgcggcagc ggttgtcacc ttcagcgttg gcgccatttc cgccatgaac gccctcggcg    5460
gcgcctatgc cgaaaacctg ccggttatcc tgatttccgg cgcgcccaac agcaatgatc    5520
agggcacagg tcatatcctg catcacacaa tcggcaagac ggattacagc taccagcttg    5580
aaatggcccg tcaggtcacc tgtgccgccg aaagcattac cgacgctcac tccgccccgg    5640
ccaagattga ccacgtcatt cgcacggcgc tgcgcgagcg taagccggcc tatctggaca    5700
tcgcgtgcaa cattgcctcc gagccctgcg tgcggcctgg ccctgtcagc agcctgctgt    5760
ccgagcctga aatcgaccac acgagcctga aggccgcagt ggacgccacg gttgccttgc    5820
tggaaaaatc ggccagcccc gtcatgctgc tgggcagcaa gctgcgggcc gccaacgcac    5880
tggccgcaac cgaaacgctg gcagacaagc tgcaatgcgc ggtgaccatc atggcggccg    5940
cgaaaggctt tttccccgaa gaccacgcgg gtttcgcgcg cctgtactgg ggcgaagtct    6000
cgaaccccgg cgtgcaggaa ctggtggaga cctccgacgc actgctgtgc atcgcccccg    6060
tattcaacga ctattcaaca gtcggctggt cggcatggcc caagggcccc aatgtgattc    6120
tggctgagcc cgaccgcgta acggtcgatg ccgcgcccta tgacggcttt accctgcgcg    6180
ccttcctgca ggctctggcg gaaaaagccc ccgcgcgccc ggcctccgca cagaaaagca    6240
gcgtcccgac gtgctcgctc accgcgacat ccgatgaagc cggtctgacg aatgacgaaa    6300
tcgtccgtca tatcaacgcc ctgctgacat caaacacgac gctggtggca gaaaccggcg    6360
attcatggtt caatgccatg cgcatgaccc tgccgcgcgg tgcgcgcgtg gaactggaaa    6420
tgcagtgggg ccatatcggc tggtccgtgc cctccgcctt cggcaatgcc atgggctcgc    6480
aggaccgcca gcatgtggtg atggtaggcg atggctcctt ccagcttacc gcgcaggaag    6540
tggctcagat ggtgcgctac gaactgcccg tcattatctt tctgatcaac aaccgtggct    6600
atgtcggtgg catcgccatt catgacggcc cgtacaacta tatcaagaac tgggattacg    6660
ccggcctgat ggaagtcttc aacgccgag aaggccatgg acttggcctg aaagccacca    6720
ccccgaagga actgacagaa gccatcgcca gggcaaaagc caatacccgc ggcccgacgc    6780
tgatcgaatg ccagatcgac cgcacggact gcacggatat gctggttcaa tggggccgca    6840
aggttgcctc aaccaacgcg cgcaagacca ctctggccct cgagcaccac caccaccacc    6900
actgagatcc ggctgctaac aaagcccgaa aggaagctga gttggctgct gccaccgctg    6960
```

```
agcaataact agcataaccc cttggggcct ctaaacgggt cttgaggggt tttttgctga      7020
aaggaggaac tatatccgga t                                                7041
```

<210> SEQ ID NO 6
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: n is a, c, g, or t

<400> SEQUENCE: 6

```
ccgtggctat gtcndtggca tcgccattc                                          29
```

<210> SEQ ID NO 7
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: n is a, c, g, or t

<400> SEQUENCE: 7

```
gaatggcgat gccahngaca tagccacgg                                          29
```

<210> SEQ ID NO 8
<211> LENGTH: 1680
<212> TYPE: DNA
<213> ORGANISM: Artificial Sequence
<220> FEATURE:
<223> OTHER INFORMATION: Synthetic

<400> SEQUENCE: 8

```
atgacctata ctgttggcat gtatcttgca gaacgccttg tacagatcgg gctgaagcat        60
cacttcgccg tggcgggcga ctacaatctc gttcttctgg atcagttgct cctcaacaag       120
gacatgaaac agatctattg ctgcaatgag ttgaactgtg gcttcagcgc ggaaggctac       180
gcccgttcta acggggctgc ggcagcggtt gtcaccttca gcgttggcgc catttccgcc       240
atgaacgccc tcggcggcgc ctatgccgaa aacctgccgg ttatcctgat ttccggcgcg       300
cccaacagca atgatcaggg cacaggtcat atcctgcatc acacaatcgg caagacggat       360
tacagctacc agcttgaaat ggcccgtcag gtcacctgtg ccgccgaaag cattaccgac       420
gctcactccg ccccggccaa gattgaccac gtcattcgca cggcgctgcg cgagcgtaag       480
ccggcctatc tggacatcgc gtgcaacatt gcctccgagc cctgcgtgcg gcctggccct       540
gtcagcagcc tgctgtccga gcctgaaatc gaccacacga gcctgaaggc cgcagtggac       600
gccacggttg ccttgctgga aaaatcggcc agcccgtca tgctgctggg cagcaagctg       660
cgggccgcca acgcactggc cgcaaccgaa acgctggcag acaagctgca atgcgcggtg       720
accatcatgg cggccgcgaa aggcttttc cccgaagacc acgcgggttt ccgcggcctg       780
tactggggcg aagtctcgaa ccccggcgtg caggaactgg tggagacctc cgacgcactg       840
ctgtgcatcg ccccgtatt caacgactat tcaacagtcg gctggtcggc atggcccaag       900
ggccccaatg tgattctggc tgagcccgac cgcgtaacgg tcgatggccg cgcctatgac       960
```

```
ggctttaccc tgcgcgcctt cctgcaggct ctggcggaaa agcccccgc gcgcccggcc   1020 tccgcacaga aaagcagcgt cccgacgtgc tcgctcaccg cgacatccga tgaagccggt   1080
ctgacgaatg acgaaatcgt ccgtcatatc aacgccctgc tgacatcaaa cacgacgctg   1140
gtggcagaaa ccggcgattc atggttcaat gccatgcgca tgaccctgcc gcgcggtgcg   1200
cgcgtggaac tggaaatgca gtggggccat atcggctggt ccgtgccctc cgccttcggc   1260
aatgccatgg gctcgcagga ccgccagcat gtggtgatgg taggcgatgg ctccttccag   1320
cttaccgcgc aggaagtggc tcagatggtg cgctacgaac tgcccgtcat tatctttctg   1380
atcaacaacc gtggctatgt cattggcatc gccattcatg acggcccgta caactatatc   1440
aagaactggg attacgccgg cctgatggaa gtcttcaacg ccggagaagg ccatggactt   1500
ggcctgaaag ccaccacccc gaaggaactg acagaagcca tcgccagggc aaaagccaat   1560
acccgcggcc cgacgctgat cgaatgccag atcgaccgca cggactgcac ggatatgctg   1620
gttcaatggg ccgcaaggt tgcctcaacc aacgcgcgca agaccactct ggccctcgag   1680
```

<210> SEQ ID NO 9
<211> LENGTH: 560
<212> TYPE: PRT
<213> ORGANISM: Artificial Sequence
<220> FEATURE:
<223> OTHER INFORMATION: Synthetic

<400> SEQUENCE: 9

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240
```

```
Thr Ile Met Ala Ala Ala Lys Gly Phe Phe Pro Glu Asp His Ala Gly
            245                 250                 255

Phe Arg Gly Leu Tyr Trp Gly Glu Val Ser Asn Pro Gly Val Gln Glu
        260                 265                 270

Leu Val Glu Thr Ser Asp Ala Leu Leu Cys Ile Ala Pro Val Phe Asn
    275                 280                 285

Asp Tyr Ser Thr Val Gly Trp Ser Ala Trp Pro Lys Gly Pro Asn Val
290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
    450                 455                 460

Gly Tyr Val Gly Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln His Gly
    530                 535                 540

Arg Lys Val Ala Ser Thr Asn Ala Arg Lys Thr Thr Leu Ala Leu Glu
545                 550                 555                 560

<210> SEQ ID NO 10
<211> LENGTH: 560
<212> TYPE: PRT
<213> ORGANISM: Artificial Sequence
<220> FEATURE:
<223> OTHER INFORMATION: Synthetic

<400> SEQUENCE: 10

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45
```

```
Asn Glu Leu Asn Cys Gly Phe Ser Ala Glu Gly Tyr Ala Arg Ser Asn
     50                  55                  60

Gly Ala Ala Ala Val Val Thr Phe Ser Val Gly Ala Ile Ser Ala
 65              70                  75                  80

Met Asn Ala Leu Gly Gly Ala Tyr Ala Glu Asn Leu Pro Val Ile Leu
             85                  90                  95

Ile Ser Gly Ala Pro Asn Ser Asn Asp Gln Gly Thr Gly His Ile Leu
         100                 105                 110

His His Thr Ile Gly Lys Thr Asp Tyr Ser Tyr Gln Leu Glu Met Ala
         115                 120                 125

Arg Gln Val Thr Cys Ala Ala Glu Ser Ile Thr Asp Ala His Ser Ala
         130                 135                 140

Pro Ala Lys Ile Asp His Val Ile Arg Thr Ala Leu Arg Glu Arg Lys
145             150                 155                 160

Pro Ala Tyr Leu Asp Ile Ala Cys Asn Ile Ala Ser Glu Pro Cys Val
             165                 170                 175

Arg Pro Gly Pro Val Ser Ser Leu Leu Ser Glu Pro Glu Ile Asp His
             180                 185                 190

Thr Ser Leu Lys Ala Ala Val Asp Ala Thr Val Ala Leu Leu Glu Lys
             195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
             245                 250                 255

Phe Arg Gly Leu Tyr Trp Gly Glu Val Ser Asn Pro Gly Val Gln Glu
             260                 265                 270

Leu Val Glu Thr Ser Asp Ala Leu Leu Cys Ile Ala Pro Val Phe Asn
         275                 280                 285

Asp Tyr Ser Thr Val Gly Trp Ser Ala Trp Pro Lys Gly Pro Asn Val
         290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
             325                 330                 335

Ala Arg Pro Ala Ser Ala Gln Lys Ser Ser Val Pro Thr Cys Ser Leu
             340                 345                 350

Thr Ala Thr Ser Asp Glu Ala Gly Leu Thr Asn Asp Glu Ile Val Arg
             355                 360                 365

His Ile Asn Ala Leu Leu Thr Ser Asn Thr Thr Leu Val Ala Glu Thr
         370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
             405                 410                 415

Ser Ala Phe Gly Asn Ala Met Gly Ser Gln Asp Arg Gln His Val Val
             420                 425                 430

Met Val Gly Asp Gly Ser Phe Gln Leu Thr Ala Gln Glu Val Ala Gln
             435                 440                 445

Met Val Arg Tyr Glu Leu Pro Val Ile Ile Phe Leu Ile Asn Asn Arg
     450                 455                 460

Gly Tyr Val Gly Gly Ile Ala Ile His Asp Gly Pro Tyr Asn Tyr Ile
```

```
                465                 470                 475                 480
Lys Asn Trp Asp Tyr Ala Gly Leu Met Glu Val Phe Asn Ala Gly Glu
                    485                 490                 495

Gly His Gly Leu Gly Leu Lys Ala Thr Thr Pro Lys Glu Leu Thr Glu
                500                 505                 510

Ala Ile Ala Arg Ala Lys Ala Asn Thr Arg Gly Pro Thr Leu Ile Glu
                515                 520                 525

Cys Gln Ile Asp Arg Thr Asp Cys Thr Asp Met Leu Val Gln Phe Gly
                530                 535                 540

Arg Lys Val Ala Ser Thr Asn Ala Arg Lys Thr Thr Leu Ala Leu Glu
545                 550                 555                 560

<210> SEQ ID NO 11
<211> LENGTH: 560
<212> TYPE: PRT
<213> ORGANISM: Artificial Sequence
<220> FEATURE:
<223> OTHER INFORMATION: Synthetic

<400> SEQUENCE: 11

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
```

```
            275                 280                 285
Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
    450                 455                 460

Gly Tyr Val Gly Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Pro Gly
    530                 535                 540

Arg Lys Val Ala Ser Thr Asn Ala Arg Lys Thr Thr Leu Ala Leu Glu
545                 550                 555                 560

<210> SEQ ID NO 12
<211> LENGTH: 560
<212> TYPE: PRT
<213> ORGANISM: Artificial Sequence
<220> FEATURE:
<223> OTHER INFORMATION: Synthetic

<400> SEQUENCE: 12

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
```

```
                           85                  90                  95
Ile Ser Gly Ala Pro Asn Ser Asn Asp Gln Gly Thr Gly His Ile Leu
                100                 105                 110
His His Thr Ile Gly Lys Thr Asp Tyr Ser Tyr Gln Leu Glu Met Ala
        115                 120                 125
Arg Gln Val Thr Cys Ala Ala Glu Ser Ile Thr Asp Ala His Ser Ala
    130                 135                 140
Pro Ala Lys Ile Asp His Val Ile Arg Thr Ala Leu Arg Glu Arg Lys
145                 150                 155                 160
Pro Ala Tyr Leu Asp Ile Ala Cys Asn Ile Ala Ser Glu Pro Cys Val
                165                 170                 175
Arg Pro Gly Pro Val Ser Ser Leu Leu Ser Glu Pro Glu Ile Asp His
            180                 185                 190
Thr Ser Leu Lys Ala Ala Val Asp Ala Thr Val Ala Leu Leu Glu Lys
                195                 200                 205
Ser Ala Ser Pro Val Met Leu Leu Gly Ser Lys Leu Arg Ala Ala Asn
    210                 215                 220
Ala Leu Ala Ala Thr Glu Thr Leu Ala Asp Lys Leu Gln Cys Ala Val
225                 230                 235                 240
Thr Ile Met Ala Ala Lys Gly Phe Phe Pro Glu Asp His Ala Gly
                245                 250                 255
Phe Arg Gly Leu Tyr Trp Gly Glu Val Ser Asn Pro Gly Val Gln Glu
            260                 265                 270
Leu Val Glu Thr Ser Asp Ala Leu Leu Cys Ile Ala Pro Val Phe Asn
                275                 280                 285
Asp Tyr Ser Thr Val Gly Trp Ser Ala Trp Pro Lys Gly Pro Asn Val
    290                 295                 300
Ile Leu Ala Glu Pro Asp Arg Val Thr Val Asp Gly Arg Ala Tyr Asp
305                 310                 315                 320
Gly Phe Thr Leu Arg Ala Phe Leu Gln Ala Leu Ala Glu Lys Ala Pro
                325                 330                 335
Ala Arg Pro Ala Ser Ala Gln Lys Ser Ser Val Pro Thr Cys Ser Leu
            340                 345                 350
Thr Ala Thr Ser Asp Glu Ala Gly Leu Thr Asn Asp Glu Ile Val Arg
                355                 360                 365
His Ile Asn Ala Leu Leu Thr Ser Asn Thr Thr Leu Val Ala Glu Thr
    370                 375                 380
Gly Asp Ser Trp Phe Asn Ala Met Arg Met Thr Leu Pro Arg Gly Ala
385                 390                 395                 400
Arg Val Glu Leu Glu Met Gln Trp Gly His Ile Gly Trp Ser Val Pro
                405                 410                 415
Ser Ala Phe Gly Asn Ala Met Gly Ser Gln Asp Arg Gln His Val Val
            420                 425                 430
Met Val Gly Asp Gly Ser Phe Gln Leu Thr Ala Gln Glu Val Ala Gln
                435                 440                 445
Met Val Arg Tyr Glu Leu Pro Val Ile Ile Phe Leu Ile Asn Asn Arg
    450                 455                 460
Gly Tyr Val Gly Gly Ile Ala Ile His Asp Gly Pro Tyr Asn Tyr Ile
465                 470                 475                 480
Lys Asn Trp Asp Tyr Ala Gly Leu Met Glu Val Phe Asn Ala Gly Glu
                485                 490                 495
Gly His Gly Leu Gly Leu Lys Ala Thr Thr Pro Lys Glu Leu Thr Glu
            500                 505                 510
```

```
Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Ile Gly
    530                 535                 540

Arg Lys Val Ala Ser Thr Asn Ala Arg Lys Thr Thr Leu Ala Leu Glu
545                 550                 555                 560

<210> SEQ ID NO 13
<211> LENGTH: 560
<212> TYPE: PRT
<213> ORGANISM: Artificial Sequence
<220> FEATURE:
<223> OTHER INFORMATION: Synthetic

<400> SEQUENCE: 13

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320
```

```
Gly Phe Thr Leu Arg Ala Phe Leu Gln Ala Leu Ala Glu Lys Ala Pro
            325                 330                 335

Ala Arg Pro Ala Ser Ala Gln Lys Ser Ser Val Pro Thr Cys Ser Leu
        340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
    450                 455                 460

Gly Tyr Val Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Leu Gly
    530                 535                 540

Arg Lys Val Ala Ser Thr Asn Ala Arg Lys Thr Thr Leu Ala Leu Glu
545                 550                 555                 560

<210> SEQ ID NO 14
<211> LENGTH: 560
<212> TYPE: PRT
<213> ORGANISM: Artificial Sequence
<220> FEATURE:
<223> OTHER INFORMATION: Synthetic

<400> SEQUENCE: 14

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125
```

-continued

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Phe Leu Ile Asn Asn Arg
450                 455                 460

Gly Tyr Val Gly Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Met Gly
530                 535                 540

Arg Lys Val Ala Ser Thr Asn Ala Arg Lys Thr Thr Leu Ala Leu Glu
545                 550                 555                 560

<210> SEQ ID NO 15
<211> LENGTH: 560
<212> TYPE: PRT
<213> ORGANISM: Artificial Sequence
<220> FEATURE:
<223> OTHER INFORMATION: Synthetic

<400> SEQUENCE: 15

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
    115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
    195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
    275                 280                 285

Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

-continued

```
Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
    450                 455                 460

Gly Tyr Val Gly Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Val Gly
    530                 535                 540

Arg Lys Val Ala Ser Thr Asn Ala Arg Lys Thr Thr Leu Ala Leu Glu
545                 550                 555                 560
```

<210> SEQ ID NO 16
<211> LENGTH: 560
<212> TYPE: PRT
<213> ORGANISM: Artificial Sequence
<220> FEATURE:
<223> OTHER INFORMATION: Synthetic

<400> SEQUENCE: 16

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160
```

Pro Ala Tyr Leu Asp Ile Ala Cys Asn Ile Ala Ser Glu Pro Cys Val
            165                 170                 175

Arg Pro Gly Pro Val Ser Ser Leu Leu Ser Glu Pro Glu Ile Asp His
        180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Phe Leu Ile Asn Asn Arg
    450                 455                 460

Gly Tyr Val Gly Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Ala Gly
    530                 535                 540

Arg Lys Val Ala Ser Thr Asn Ala Arg Lys Thr Thr Leu Ala Leu Glu
545                 550                 555                 560

<210> SEQ ID NO 17
<211> LENGTH: 560
<212> TYPE: PRT

<213> ORGANISM: Artificial Sequence
<220> FEATURE:
<223> OTHER INFORMATION: Synthetic

<400> SEQUENCE: 17

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
370                 375                 380

Gly Asp Ser Trp Phe Asn Ala Met Arg Met Thr Leu Pro Arg Gly Ala

```
                385                 390                 395                 400
Arg Val Glu Leu Glu Met Gln Trp Gly His Ile Gly Trp Ser Val Pro
                    405                 410                 415

Ser Ala Phe Gly Asn Ala Met Gly Ser Gln Asp Arg Gln His Val Val
                420                 425                 430

Met Val Gly Asp Gly Ser Phe Gln Leu Thr Ala Gln Glu Val Ala Gln
                435                 440                 445

Met Val Arg Tyr Glu Leu Pro Val Ile Ile Phe Leu Ile Asn Asn Arg
            450                 455                 460

Gly Tyr Val Gly Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
                500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Tyr Gly
            530                 535                 540

Arg Lys Val Ala Ser Thr Asn Ala Arg Lys Thr Leu Ala Leu Glu
545                 550                 555                 560

<210> SEQ ID NO 18
<211> LENGTH: 560
<212> TYPE: PRT
<213> ORGANISM: Artificial Sequence
<220> FEATURE:
<223> OTHER INFORMATION: Synthetic

<400> SEQUENCE: 18

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
        50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
```

```
                195                 200                 205
Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Val Ser Asn Pro Gly Val Gln Glu
                260                 265                 270

Leu Val Glu Thr Ser Asp Ala Leu Leu Cys Ile Ala Pro Val Phe Asn
                275                 280                 285

Asp Tyr Ser Thr Val Gly Trp Ser Ala Trp Pro Lys Gly Pro Asn Val
290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
                340                 345                 350

Thr Ala Thr Ser Asp Glu Ala Gly Leu Thr Asn Asp Glu Ile Val Arg
                355                 360                 365

His Ile Asn Ala Leu Leu Thr Ser Asn Thr Thr Leu Val Ala Glu Thr
370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
                420                 425                 430

Met Val Gly Asp Gly Ser Phe Gln Leu Thr Ala Gln Glu Val Ala Gln
                435                 440                 445

Met Val Arg Tyr Glu Leu Pro Val Ile Ile Phe Leu Ile Asn Asn Arg
450                 455                 460

Gly Tyr Val Gly Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
                500                 505                 510

Ala Ile Ala Arg Ala Lys Ala Asn Thr Arg Gly Pro Thr Leu Ile Glu
                515                 520                 525

Cys Gln Ile Asp Arg Thr Asp Cys Thr Asp Met Leu Val Gln Thr Gly
                530                 535                 540

Arg Lys Val Ala Ser Thr Asn Ala Arg Lys Thr Thr Leu Ala Leu Glu
545                 550                 555                 560

<210> SEQ ID NO 19
<211> LENGTH: 560
<212> TYPE: PRT
<213> ORGANISM: Artificial Sequence
<220> FEATURE:
<223> OTHER INFORMATION: Synthetic

<400> SEQUENCE: 19

Met Thr Tyr Thr Val Gly Met Tyr Leu Ala Glu Arg Leu Val Gln Ile
```

-continued

```
1               5               10              15
Gly Leu Lys His His Phe Ala Val Ala Gly Asp Tyr Asn Leu Val Leu
            20              25              30
Leu Asp Gln Leu Leu Asn Lys Asp Met Lys Gln Ile Tyr Cys Cys
        35              40              45
Asn Glu Leu Asn Cys Gly Phe Ser Ala Glu Gly Tyr Ala Arg Ser Asn
    50              55              60
Gly Ala Ala Ala Val Val Thr Phe Ser Val Gly Ala Ile Ser Ala
65              70              75              80
Met Asn Ala Leu Gly Gly Ala Tyr Ala Glu Asn Leu Pro Val Ile Leu
                85              90              95
Ile Ser Gly Ala Pro Asn Ser Asn Asp Gln Gly Thr Gly His Ile Leu
            100             105             110
His His Thr Ile Gly Lys Thr Asp Tyr Ser Tyr Gln Leu Glu Met Ala
        115             120             125
Arg Gln Val Thr Cys Ala Ala Glu Ser Ile Thr Asp Ala His Ser Ala
    130             135             140
Pro Ala Lys Ile Asp His Val Ile Arg Thr Ala Leu Arg Glu Arg Lys
145             150             155             160
Pro Ala Tyr Leu Asp Ile Ala Cys Asn Ile Ala Ser Glu Pro Cys Val
                165             170             175
Arg Pro Gly Pro Val Ser Ser Leu Leu Ser Glu Pro Glu Ile Asp His
            180             185             190
Thr Ser Leu Lys Ala Ala Val Asp Ala Thr Val Ala Leu Leu Glu Lys
        195             200             205
Ser Ala Ser Pro Val Met Leu Leu Gly Ser Lys Leu Arg Ala Ala Asn
    210             215             220
Ala Leu Ala Ala Thr Glu Thr Leu Ala Asp Lys Leu Gln Cys Ala Val
225             230             235             240
Thr Ile Met Ala Ala Lys Gly Phe Phe Pro Glu Asp His Ala Gly
                245             250             255
Phe Arg Gly Leu Tyr Trp Gly Glu Val Ser Asn Pro Gly Val Gln Glu
            260             265             270
Leu Val Glu Thr Ser Asp Ala Leu Leu Cys Ile Ala Pro Val Phe Asn
        275             280             285
Asp Tyr Ser Thr Val Gly Trp Ser Ala Trp Pro Lys Gly Pro Asn Val
    290             295             300
Ile Leu Ala Glu Pro Asp Arg Val Thr Val Asp Gly Arg Ala Tyr Asp
305             310             315             320
Gly Phe Thr Leu Arg Ala Phe Leu Gln Ala Leu Ala Glu Lys Ala Pro
                325             330             335
Ala Arg Pro Ala Ser Ala Gln Lys Ser Ser Val Pro Thr Cys Ser Leu
            340             345             350
Thr Ala Thr Ser Asp Glu Ala Gly Leu Thr Asn Asp Glu Ile Val Arg
        355             360             365
His Ile Asn Ala Leu Leu Thr Ser Asn Thr Thr Leu Val Ala Glu Thr
    370             375             380
Gly Asp Ser Trp Phe Asn Ala Met Arg Met Thr Leu Pro Arg Gly Ala
385             390             395             400
Arg Val Glu Leu Glu Met Gln Trp Gly His Ile Gly Trp Ser Val Pro
                405             410             415
Ser Ala Phe Gly Asn Ala Met Gly Ser Gln Asp Arg Gln His Val Val
            420             425             430
```

Met Val Gly Asp Gly Ser Phe Gln Leu Thr Ala Gln Glu Val Ala Gln
              435                 440                 445

Met Val Arg Tyr Glu Leu Pro Val Ile Ile Phe Leu Ile Asn Asn Arg
450                 455                 460

Gly Tyr Val Gly Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
              485                 490                 495

Gly His Gly Leu Gly Leu Lys Ala Thr Thr Pro Lys Glu Leu Thr Glu
              500                 505                 510

Ala Ile Ala Arg Ala Lys Ala Asn Thr Arg Gly Pro Thr Leu Ile Glu
              515                 520                 525

Cys Gln Ile Asp Arg Thr Asp Cys Thr Asp Met Leu Val Gln Gly Gly
              530                 535                 540

Arg Lys Val Ala Ser Thr Asn Ala Arg Lys Thr Thr Leu Ala Leu Glu
545                 550                 555                 560

<210> SEQ ID NO 20
<211> LENGTH: 560
<212> TYPE: PRT
<213> ORGANISM: Artificial Sequence
<220> FEATURE:
<223> OTHER INFORMATION: Synthetic

<400> SEQUENCE: 20

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
              20                  25                  30

Leu Asp Gln Leu Leu Leu Asn Lys Asp Met Lys Gln Ile Tyr Cys Cys
              35                  40                  45

Asn Glu Leu Asn Cys Gly Phe Ser Ala Glu Gly Tyr Ala Arg Ser Asn
          50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
              85                  90                  95

Ile Ser Gly Ala Pro Asn Ser Asn Asp Gln Gly Thr Gly His Ile Leu
          100                 105                 110

His His Thr Ile Gly Lys Thr Asp Tyr Ser Tyr Gln Leu Glu Met Ala
          115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
              165                 170                 175

Arg Pro Gly Pro Val Ser Ser Leu Leu Ser Glu Pro Glu Ile Asp His
          180                 185                 190

Thr Ser Leu Lys Ala Ala Val Asp Ala Thr Val Ala Leu Leu Glu Lys
          195                 200                 205

Ser Ala Ser Pro Val Met Leu Leu Gly Ser Lys Leu Arg Ala Ala Asn
          210                 215                 220

Ala Leu Ala Ala Thr Glu Thr Leu Ala Asp Lys Leu Gln Cys Ala Val
225                 230                 235                 240

```
Thr Ile Met Ala Ala Ala Lys Gly Phe Phe Pro Glu Asp His Ala Gly
            245                 250                 255

Phe Arg Gly Leu Tyr Trp Gly Glu Val Ser Asn Pro Gly Val Gln Glu
        260                 265                 270

Leu Val Glu Thr Ser Asp Ala Leu Leu Cys Ile Ala Pro Val Phe Asn
            275                 280                 285

Asp Tyr Ser Thr Val Gly Trp Ser Ala Trp Pro Lys Gly Pro Asn Val
        290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
            325                 330                 335

Ala Arg Pro Ala Ser Ala Gln Lys Ser Ser Val Pro Thr Cys Ser Leu
        340                 345                 350

Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
        370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
            405                 410                 415

Ser Ala Phe Gly Asn Ala Met Gly Ser Gln Asp Arg Gln His Val Val
        420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
        450                 455                 460

Gly Tyr Val Gly Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
            485                 490                 495

Gly His Gly Leu Gly Leu Lys Ala Thr Thr Pro Lys Glu Leu Thr Glu
        500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Ser Gly
        530                 535                 540

Arg Lys Val Ala Ser Thr Asn Ala Arg Lys Thr Thr Leu Ala Leu Glu
545                 550                 555                 560

<210> SEQ ID NO 21
<211> LENGTH: 560
<212> TYPE: PRT
<213> ORGANISM: Artificial Sequence
<220> FEATURE:
<223> OTHER INFORMATION: Synthetic

<400> SEQUENCE: 21

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45
```

```
Asn Glu Leu Asn Cys Gly Phe Ser Ala Glu Gly Tyr Ala Arg Ser Asn
     50                  55                  60
Gly Ala Ala Ala Val Val Thr Phe Ser Val Gly Ala Ile Ser Ala
 65              70                  75                  80
Met Asn Ala Leu Gly Gly Ala Tyr Ala Glu Asn Leu Pro Val Ile Leu
                 85                  90                  95
Ile Ser Gly Ala Pro Asn Ser Asn Asp Gln Gly Thr Gly His Ile Leu
                100                 105                 110
His His Thr Ile Gly Lys Thr Asp Tyr Ser Tyr Gln Leu Glu Met Ala
            115                 120                 125
Arg Gln Val Thr Cys Ala Ala Glu Ser Ile Thr Asp Ala His Ser Ala
    130                 135                 140
Pro Ala Lys Ile Asp His Val Ile Arg Thr Ala Leu Arg Glu Arg Lys
145                 150                 155                 160
Pro Ala Tyr Leu Asp Ile Ala Cys Asn Ile Ala Ser Glu Pro Cys Val
                165                 170                 175
Arg Pro Gly Pro Val Ser Ser Leu Leu Ser Glu Pro Glu Ile Asp His
            180                 185                 190
Thr Ser Leu Lys Ala Ala Val Asp Ala Thr Val Ala Leu Leu Glu Lys
        195                 200                 205
Ser Ala Ser Pro Val Met Leu Leu Gly Ser Lys Leu Arg Ala Ala Asn
210                 215                 220
Ala Leu Ala Ala Thr Glu Thr Leu Ala Asp Lys Leu Gln Cys Ala Val
225                 230                 235                 240
Thr Ile Met Ala Ala Lys Gly Phe Phe Pro Glu Asp His Ala Gly
                245                 250                 255
Phe Arg Gly Leu Tyr Trp Gly Glu Val Ser Asn Pro Gly Val Gln Glu
            260                 265                 270
Leu Val Glu Thr Ser Asp Ala Leu Leu Cys Ile Ala Pro Val Phe Asn
        275                 280                 285
Asp Tyr Ser Thr Val Gly Trp Ser Ala Trp Pro Lys Gly Pro Asn Val
    290                 295                 300
Ile Leu Ala Glu Pro Asp Arg Val Thr Val Asp Gly Arg Ala Tyr Asp
305                 310                 315                 320
Gly Phe Thr Leu Arg Ala Phe Leu Gln Ala Leu Ala Glu Lys Ala Pro
                325                 330                 335
Ala Arg Pro Ala Ser Ala Gln Lys Ser Ser Val Pro Thr Cys Ser Leu
            340                 345                 350
Thr Ala Thr Ser Asp Glu Ala Gly Leu Thr Asn Asp Glu Ile Val Arg
        355                 360                 365
His Ile Asn Ala Leu Leu Thr Ser Asn Thr Thr Leu Val Ala Glu Thr
    370                 375                 380
Gly Asp Ser Trp Phe Asn Ala Met Arg Met Thr Leu Pro Arg Gly Ala
385                 390                 395                 400
Arg Val Glu Leu Glu Met Gln Trp Gly His Ile Gly Trp Ser Val Pro
                405                 410                 415
Ser Ala Phe Gly Asn Ala Met Gly Ser Gln Asp Arg Gln His Val Val
            420                 425                 430
Met Val Gly Asp Gly Ser Phe Gln Leu Thr Ala Gln Glu Val Ala Gln
        435                 440                 445
Met Val Arg Tyr Glu Leu Pro Val Ile Ile Phe Leu Ile Asn Asn Arg
    450                 455                 460
```

```
Gly Tyr Val Gly Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
            485                 490                 495

Gly His Gly Leu Gly Leu Lys Ala Thr Thr Pro Lys Glu Leu Thr Glu
        500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Cys Gly
        530                 535                 540

Arg Lys Val Ala Ser Thr Asn Ala Arg Lys Thr Thr Leu Ala Leu Glu
545                 550                 555                 560

<210> SEQ ID NO 22
<211> LENGTH: 560
<212> TYPE: PRT
<213> ORGANISM: Artificial Sequence
<220> FEATURE:
<223> OTHER INFORMATION: Synthetic

<400> SEQUENCE: 22

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270
```

-continued

```
Leu Val Glu Thr Ser Asp Ala Leu Cys Ile Ala Pro Val Phe Asn
            275                 280                 285

Asp Tyr Ser Thr Val Gly Trp Ser Ala Trp Pro Lys Gly Pro Asn Val
290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
    450                 455                 460

Gly Tyr Val Ala Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln His Gly
    530                 535                 540

Arg Lys Val Ala Ser Thr Asn Ala Arg Lys Thr Thr Leu Ala Leu Glu
545                 550                 555                 560

<210> SEQ ID NO 23
<211> LENGTH: 560
<212> TYPE: PRT
<213> ORGANISM: Artificial Sequence
<220> FEATURE:
<223> OTHER INFORMATION: Synthetic

<400> SEQUENCE: 23

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
        50                  55                  60

Gly Ala Ala Ala Ala Val Val Thr Phe Ser Val Gly Ala Ile Ser Ala
65                  70                  75                  80
```

```
Met Asn Ala Leu Gly Ala Tyr Ala Glu Asn Leu Pro Val Ile Leu
             85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
            115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
            195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
            275                 280                 285

Asp Tyr Ser Thr Val Gly Trp Ser Ala Trp Pro Lys Gly Pro Asn Val
            290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
            370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
450                 455                 460

Gly Tyr Val Ala Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
```

```
                500                 505                 510
Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Phe Gly
            530                 535                 540

Arg Lys Val Ala Ser Thr Asn Ala Arg Lys Thr Leu Ala Leu Glu
545                 550                 555                 560

<210> SEQ ID NO 24
<211> LENGTH: 560
<212> TYPE: PRT
<213> ORGANISM: Artificial Sequence
<220> FEATURE:
<223> OTHER INFORMATION: Synthetic

<400> SEQUENCE: 24

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
290                 295                 300

Ile Leu Ala Glu Pro Asp Arg Val Thr Val Asp Gly Arg Ala Tyr Asp
```

Gly Phe Thr Leu Arg Ala Phe Leu Gln Ala Leu Ala Glu Lys Ala Pro
305                 310                 315                 320

Ala Arg Pro Ala Ser Ala Gln Lys Ser Ser Val Pro Thr Cys Ser Leu
            325                 330                 335

Thr Ala Thr Ser Asp Glu Ala Gly Leu Thr Asn Asp Glu Ile Val Arg
        340                 345                 350

His Ile Asn Ala Leu Leu Thr Ser Asn Thr Thr Leu Val Ala Glu Thr
    355                 360                 365

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
            405                 410                 415

Ser Ala Phe Gly Asn Ala Met Gly Ser Gln Asp Arg Gln His Val Val
        420                 425                 430

Met Val Gly Asp Gly Ser Phe Gln Leu Thr Ala Gln Glu Val Ala Gln
    435                 440                 445

Met Val Arg Tyr Glu Leu Pro Val Ile Ile Phe Leu Ile Asn Asn Arg
450                 455                 460

Gly Tyr Val Ala Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
            485                 490                 495

Gly His Gly Leu Gly Leu Lys Ala Thr Thr Pro Lys Glu Leu Thr Glu
        500                 505                 510

Ala Ile Ala Arg Ala Lys Ala Asn Thr Arg Gly Pro Thr Leu Ile Glu
    515                 520                 525

Cys Gln Ile Asp Arg Thr Asp Cys Thr Asp Met Leu Val Gln Pro Gly
530                 535                 540

Arg Lys Val Ala Ser Thr Asn Ala Arg Lys Thr Thr Leu Ala Leu Glu
545                 550                 555                 560

<210> SEQ ID NO 25
<211> LENGTH: 560
<212> TYPE: PRT
<213> ORGANISM: Artificial Sequence
<220> FEATURE:
<223> OTHER INFORMATION: Synthetic

<400> SEQUENCE: 25

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
            85                  90                  95

Ile Ser Gly Ala Pro Asn Ser Asn Asp Gln Gly Thr Gly His Ile Leu
        100                 105                 110

His His Thr Ile Gly Lys Thr Asp Tyr Ser Tyr Gln Leu Glu Met Ala

-continued

```
            115                 120                 125
Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
450                 455                 460

Gly Tyr Val Ala Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Ile Gly
530                 535                 540
```

Arg Lys Val Ala Ser Thr Asn Ala Arg Lys Thr Thr Leu Ala Leu Glu
545                 550                 555                 560

<210> SEQ ID NO 26
<211> LENGTH: 560
<212> TYPE: PRT
<213> ORGANISM: Artificial Sequence
<220> FEATURE:
<223> OTHER INFORMATION: Synthetic

<400> SEQUENCE: 26

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

```
Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Val Ala Gln
        435                 440                 445

Met Val Arg Tyr Glu Leu Pro Val Ile Ile Phe Leu Ile Asn Asn Arg
    450                 455                 460

Gly Tyr Val Ala Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Leu Gly
    530                 535                 540

Arg Lys Val Ala Ser Thr Asn Ala Arg Lys Thr Thr Leu Ala Leu Glu
545                 550                 555                 560

<210> SEQ ID NO 27
<211> LENGTH: 560
<212> TYPE: PRT
<213> ORGANISM: Artificial Sequence
<220> FEATURE:
<223> OTHER INFORMATION: Synthetic

<400> SEQUENCE: 27

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160
```

```
Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
                260                 265                 270

Leu Val Glu Thr Ser Asp Ala Leu Leu Cys Ile Ala Pro Val Phe Asn
            275                 280                 285

Asp Tyr Ser Thr Val Gly Trp Ser Ala Trp Pro Lys Gly Pro Asn Val
        290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
                340                 345                 350

Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
        370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
                420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
450                 455                 460

Gly Tyr Val Ala Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
                500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Met Gly
        530                 535                 540

Arg Lys Val Ala Ser Thr Asn Ala Arg Lys Thr Thr Leu Ala Leu Glu
545                 550                 555                 560

<210> SEQ ID NO 28
<211> LENGTH: 560
```

<212> TYPE: PRT
<213> ORGANISM: Artificial Sequence
<220> FEATURE:
<223> OTHER INFORMATION: Synthetic

<400> SEQUENCE: 28

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
                260                 265                 270

Leu Val Glu Thr Ser Asp Ala Leu Leu Cys Ile Ala Pro Val Phe Asn
            275                 280                 285

Asp Tyr Ser Thr Val Gly Trp Ser Ala Trp Pro Lys Gly Pro Asn Val
        290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380

```
Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
            405                 410                 415

Ser Ala Phe Gly Asn Ala Met Gly Ser Gln Asp Arg Gln His Val Val
        420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
        450                 455                 460

Gly Tyr Val Ala Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
            485                 490                 495

Gly His Gly Leu Gly Leu Lys Ala Thr Thr Pro Lys Glu Leu Thr Glu
        500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Val Gly
        530                 535                 540

Arg Lys Val Ala Ser Thr Asn Ala Arg Lys Thr Thr Leu Ala Leu Glu
545                 550                 555                 560

<210> SEQ ID NO 29
<211> LENGTH: 560
<212> TYPE: PRT
<213> ORGANISM: Artificial Sequence
<220> FEATURE:
<223> OTHER INFORMATION: Synthetic

<400> SEQUENCE: 29

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190
```

```
Thr Ser Leu Lys Ala Ala Val Asp Ala Thr Val Ala Leu Glu Lys
    195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
            245                 250                 255

Phe Arg Gly Leu Tyr Trp Gly Glu Val Ser Asn Pro Gly Val Gln Glu
                260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
    355                 360                 365

His Ile Asn Ala Leu Leu Thr Ser Asn Thr Thr Leu Val Ala Glu Thr
370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
    435                 440                 445

Met Val Arg Tyr Glu Leu Pro Val Ile Ile Phe Leu Ile Asn Asn Arg
450                 455                 460

Gly Tyr Val Ala Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
    515                 520                 525

Cys Gln Ile Asp Arg Thr Asp Cys Thr Asp Met Leu Val Gln Ala Gly
530                 535                 540

Arg Lys Val Ala Ser Thr Asn Ala Arg Lys Thr Thr Leu Ala Leu Glu
545                 550                 555                 560

<210> SEQ ID NO 30
<211> LENGTH: 560
<212> TYPE: PRT
<213> ORGANISM: Artificial Sequence
<220> FEATURE:
<223> OTHER INFORMATION: Synthetic

<400> SEQUENCE: 30
```

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
                100                 105                 110

His His Thr Ile Gly Lys Thr Asp Tyr Ser Tyr Gln Leu Glu Met Ala
            115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
                180                 185                 190

Thr Ser Leu Lys Ala Ala Val Asp Ala Thr Val Ala Leu Leu Glu Lys
            195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
                260                 265                 270

Leu Val Glu Thr Ser Asp Ala Leu Leu Cys Ile Ala Pro Val Phe Asn
            275                 280                 285

Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
                340                 345                 350

Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
    370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
```

```
                420             425             430
Met Val Gly Asp Gly Ser Phe Gln Leu Thr Ala Gln Glu Val Ala Gln
            435             440             445

Met Val Arg Tyr Glu Leu Pro Val Ile Ile Phe Leu Ile Asn Asn Arg
            450             455             460

Gly Tyr Val Ala Gly Ile Ala Ile His Asp Gly Pro Tyr Asn Tyr Ile
465             470             475             480

Lys Asn Trp Asp Tyr Ala Gly Leu Met Glu Val Phe Asn Ala Gly Glu
            485             490             495

Gly His Gly Leu Gly Leu Lys Ala Thr Thr Pro Lys Glu Leu Thr Glu
            500             505             510

Ala Ile Ala Arg Ala Lys Ala Asn Thr Arg Gly Pro Thr Leu Ile Glu
            515             520             525

Cys Gln Ile Asp Arg Thr Asp Cys Thr Asp Met Leu Val Gln Tyr Gly
            530             535             540

Arg Lys Val Ala Ser Thr Asn Ala Arg Lys Thr Thr Leu Ala Leu Glu
545             550             555             560

<210> SEQ ID NO 31
<211> LENGTH: 560
<212> TYPE: PRT
<213> ORGANISM: Artificial Sequence
<220> FEATURE:
<223> OTHER INFORMATION: Synthetic

<400> SEQUENCE: 31

Met Thr Tyr Thr Val Gly Met Tyr Leu Ala Glu Arg Leu Val Gln Ile
1               5               10              15

Gly Leu Lys His His Phe Ala Val Ala Gly Asp Tyr Asn Leu Val Leu
            20              25              30

Leu Asp Gln Leu Leu Leu Asn Lys Asp Met Lys Gln Ile Tyr Cys Cys
            35              40              45

Asn Glu Leu Asn Cys Gly Phe Ser Ala Glu Gly Tyr Ala Arg Ser Asn
            50              55              60

Gly Ala Ala Ala Ala Val Val Thr Phe Ser Val Gly Ala Ile Ser Ala
65              70              75              80

Met Asn Ala Leu Gly Gly Ala Tyr Ala Glu Asn Leu Pro Val Ile Leu
            85              90              95

Ile Ser Gly Ala Pro Asn Ser Asn Asp Gln Gly Thr Gly His Ile Leu
            100             105             110

His His Thr Ile Gly Lys Thr Asp Tyr Ser Tyr Gln Leu Glu Met Ala
            115             120             125

Arg Gln Val Thr Cys Ala Ala Glu Ser Ile Thr Asp Ala His Ser Ala
            130             135             140

Pro Ala Lys Ile Asp His Val Ile Arg Thr Ala Leu Arg Glu Arg Lys
145             150             155             160

Pro Ala Tyr Leu Asp Ile Ala Cys Asn Ile Ala Ser Glu Pro Cys Val
            165             170             175

Arg Pro Gly Pro Val Ser Ser Leu Leu Ser Glu Pro Glu Ile Asp His
            180             185             190

Thr Ser Leu Lys Ala Ala Val Asp Ala Thr Val Ala Leu Leu Glu Lys
            195             200             205

Ser Ala Ser Pro Val Met Leu Leu Gly Ser Lys Leu Arg Ala Ala Asn
            210             215             220

Ala Leu Ala Ala Thr Glu Thr Leu Ala Asp Lys Leu Gln Cys Ala Val
```

```
            225                 230                 235                 240

Thr Ile Met Ala Ala Ala Lys Gly Phe Phe Pro Glu Asp His Ala Gly
                    245                 250                 255

Phe Arg Gly Leu Tyr Trp Gly Glu Val Ser Asn Pro Gly Val Gln Glu
                    260                 265                 270

Leu Val Glu Thr Ser Asp Ala Leu Leu Cys Ile Ala Pro Val Phe Asn
                    275                 280                 285

Asp Tyr Ser Thr Val Gly Trp Ser Ala Trp Pro Lys Gly Pro Asn Val
                    290                 295                 300

Ile Leu Ala Glu Pro Asp Arg Val Thr Val Asp Gly Arg Ala Tyr Asp
    305                 310                 315                 320

Gly Phe Thr Leu Arg Ala Phe Leu Gln Ala Leu Ala Glu Lys Ala Pro
                    325                 330                 335

Ala Arg Pro Ala Ser Ala Gln Lys Ser Ser Val Pro Thr Cys Ser Leu
                    340                 345                 350

Thr Ala Thr Ser Asp Glu Ala Gly Leu Thr Asn Asp Glu Ile Val Arg
                    355                 360                 365

His Ile Asn Ala Leu Leu Thr Ser Asn Thr Thr Leu Val Ala Glu Thr
                    370                 375                 380

Gly Asp Ser Trp Phe Asn Ala Met Arg Met Thr Leu Pro Arg Gly Ala
    385                 390                 395                 400

Arg Val Glu Leu Glu Met Gln Trp Gly His Ile Gly Trp Ser Val Pro
                    405                 410                 415

Ser Ala Phe Gly Asn Ala Met Gly Ser Gln Asp Arg Gln His Val Val
                    420                 425                 430

Met Val Gly Asp Gly Ser Phe Gln Leu Thr Ala Gln Glu Val Ala Gln
                    435                 440                 445

Met Val Arg Tyr Glu Leu Pro Val Ile Ile Phe Leu Ile Asn Asn Arg
                    450                 455                 460

Gly Tyr Val Ala Gly Ile Ala Ile His Asp Gly Pro Tyr Asn Tyr Ile
    465                 470                 475                 480

Lys Asn Trp Asp Tyr Ala Gly Leu Met Glu Val Phe Asn Ala Gly Glu
                    485                 490                 495

Gly His Gly Leu Gly Leu Lys Ala Thr Thr Pro Lys Glu Leu Thr Glu
                    500                 505                 510

Ala Ile Ala Arg Ala Lys Ala Asn Thr Arg Gly Pro Thr Leu Ile Glu
                    515                 520                 525

Cys Gln Ile Asp Arg Thr Asp Cys Thr Asp Met Leu Val Gln Thr Gly
                    530                 535                 540

Arg Lys Val Ala Ser Thr Asn Ala Arg Lys Thr Thr Leu Ala Leu Glu
    545                 550                 555                 560
```

<210> SEQ ID NO 32
<211> LENGTH: 560
<212> TYPE: PRT
<213> ORGANISM: Artificial Sequence
<220> FEATURE:
<223> OTHER INFORMATION: Synthetic

<400> SEQUENCE: 32

```
    Met Thr Tyr Thr Val Gly Met Tyr Leu Ala Glu Arg Leu Val Gln Ile
    1               5                   10                  15

Gly Leu Lys His His Phe Ala Val Ala Gly Asp Tyr Asn Leu Val Leu
                    20                  25                  30

Leu Asp Gln Leu Leu Leu Asn Lys Asp Met Lys Gln Ile Tyr Cys Cys
```

```
                 35                  40                  45
Asn Glu Leu Asn Cys Gly Phe Ser Ala Glu Gly Tyr Ala Arg Ser Asn
             50                  55                  60

Gly Ala Ala Ala Val Val Thr Phe Ser Val Gly Ala Ile Ser Ala
 65                  70                  75                  80

Met Asn Ala Leu Gly Ala Tyr Ala Glu Asn Leu Pro Val Ile Leu
                 85                  90                  95

Ile Ser Gly Ala Pro Asn Ser Asn Asp Gln Gly Thr Gly His Ile Leu
                100                 105                 110

His His Thr Ile Gly Lys Thr Asp Tyr Ser Tyr Gln Leu Glu Met Ala
             115                 120                 125

Arg Gln Val Thr Cys Ala Ala Glu Ser Ile Thr Asp Ala His Ser Ala
            130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
             180                 185                 190

Thr Ser Leu Lys Ala Ala Val Asp Ala Thr Val Ala Leu Leu Glu Lys
             195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
             260                 265                 270

Leu Val Glu Thr Ser Asp Ala Leu Leu Cys Ile Ala Pro Val Phe Asn
             275                 280                 285

Asp Tyr Ser Thr Val Gly Trp Ser Ala Trp Pro Lys Gly Pro Asn Val
             290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
             340                 345                 350

Thr Ala Thr Ser Asp Glu Ala Gly Leu Thr Asn Asp Glu Ile Val Arg
             355                 360                 365

His Ile Asn Ala Leu Leu Thr Ser Asn Thr Thr Leu Val Ala Glu Thr
             370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
             420                 425                 430

Met Val Gly Asp Gly Ser Phe Gln Leu Thr Ala Gln Glu Val Ala Gln
             435                 440                 445

Met Val Arg Tyr Glu Leu Pro Val Ile Ile Phe Leu Ile Asn Asn Arg
             450                 455                 460
```

```
Gly Tyr Val Ala Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Gly Gly
            530                 535                 540

Arg Lys Val Ala Ser Thr Asn Ala Arg Lys Thr Thr Leu Ala Leu Glu
545                 550                 555                 560

<210> SEQ ID NO 33
<211> LENGTH: 560
<212> TYPE: PRT
<213> ORGANISM: Artificial Sequence
<220> FEATURE:
<223> OTHER INFORMATION: Synthetic

<400> SEQUENCE: 33

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270
```

Leu Val Glu Thr Ser Asp Ala Leu Leu Cys Ile Ala Pro Val Phe Asn
                275                 280                 285

Asp Tyr Ser Thr Val Gly Trp Ser Ala Trp Pro Lys Gly Pro Asn Val
            290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
            370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
            450                 455                 460

Gly Tyr Val Ala Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Ser Gly
            530                 535                 540

Arg Lys Val Ala Ser Thr Asn Ala Arg Lys Thr Thr Leu Ala Leu Glu
545                 550                 555                 560

<210> SEQ ID NO 34
<211> LENGTH: 560
<212> TYPE: PRT
<213> ORGANISM: Artificial Sequence
<220> FEATURE:
<223> OTHER INFORMATION: Synthetic

<400> SEQUENCE: 34

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
        50                  55                  60

Gly Ala Ala Ala Ala Val Val Thr Phe Ser Val Gly Ala Ile Ser Ala
65                  70                  75                  80

-continued

```
Met Asn Ala Leu Gly Gly Ala Tyr Ala Glu Asn Leu Pro Val Ile Leu
                85                  90                  95
Ile Ser Gly Ala Pro Asn Ser Asn Asp Gln Gly Thr Gly His Ile Leu
                100                 105                 110
His His Thr Ile Gly Lys Thr Asp Tyr Ser Tyr Gln Leu Glu Met Ala
                115                 120                 125
Arg Gln Val Thr Cys Ala Ala Glu Ser Ile Thr Asp Ala His Ser Ala
            130                 135                 140
Pro Ala Lys Ile Asp His Val Ile Arg Thr Ala Leu Arg Glu Arg Lys
145                 150                 155                 160
Pro Ala Tyr Leu Asp Ile Ala Cys Asn Ile Ala Ser Glu Pro Cys Val
                165                 170                 175
Arg Pro Gly Pro Val Ser Ser Leu Leu Ser Glu Pro Glu Ile Asp His
                180                 185                 190
Thr Ser Leu Lys Ala Ala Val Asp Ala Thr Val Ala Leu Leu Glu Lys
                195                 200                 205
Ser Ala Ser Pro Val Met Leu Leu Gly Ser Lys Leu Arg Ala Ala Asn
            210                 215                 220
Ala Leu Ala Ala Thr Glu Thr Leu Ala Asp Lys Leu Gln Cys Ala Val
225                 230                 235                 240
Thr Ile Met Ala Ala Lys Gly Phe Phe Pro Glu Asp His Ala Gly
                245                 250                 255
Phe Arg Gly Leu Tyr Trp Gly Glu Val Ser Asn Pro Gly Val Gln Glu
                260                 265                 270
Leu Val Glu Thr Ser Asp Ala Leu Leu Cys Ile Ala Pro Val Phe Asn
                275                 280                 285
Asp Tyr Ser Thr Val Gly Trp Ser Ala Trp Pro Lys Gly Pro Asn Val
            290                 295                 300
Ile Leu Ala Glu Pro Asp Arg Val Thr Val Asp Gly Arg Ala Tyr Asp
305                 310                 315                 320
Gly Phe Thr Leu Arg Ala Phe Leu Gln Ala Leu Ala Glu Lys Ala Pro
                325                 330                 335
Ala Arg Pro Ala Ser Ala Gln Lys Ser Ser Val Pro Thr Cys Ser Leu
                340                 345                 350
Thr Ala Thr Ser Asp Glu Ala Gly Leu Thr Asn Asp Glu Ile Val Arg
            355                 360                 365
His Ile Asn Ala Leu Leu Thr Ser Asn Thr Thr Leu Val Ala Glu Thr
        370                 375                 380
Gly Asp Ser Trp Phe Asn Ala Met Arg Met Thr Leu Pro Arg Gly Ala
385                 390                 395                 400
Arg Val Glu Leu Glu Met Gln Trp Gly His Ile Gly Trp Ser Val Pro
                405                 410                 415
Ser Ala Phe Gly Asn Ala Met Gly Ser Gln Asp Arg Gln His Val Val
                420                 425                 430
Met Val Gly Asp Gly Ser Phe Gln Leu Thr Ala Gln Glu Val Ala Gln
            435                 440                 445
Met Val Arg Tyr Glu Leu Pro Val Ile Phe Leu Ile Asn Asn Arg
450                 455                 460
Gly Tyr Val Ala Gly Ile Ala Ile His Asp Gly Pro Tyr Asn Tyr Ile
465                 470                 475                 480
Lys Asn Trp Asp Tyr Ala Gly Leu Met Glu Val Phe Asn Ala Gly Glu
                485                 490                 495
```

```
Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Cys Gly
    530                 535                 540

Arg Lys Val Ala Ser Thr Asn Ala Arg Lys Thr Thr Leu Ala Leu Glu
545                 550                 555                 560

<210> SEQ ID NO 35
<211> LENGTH: 560
<212> TYPE: PRT
<213> ORGANISM: Artificial Sequence
<220> FEATURE:
<223> OTHER INFORMATION: Synthetic

<400> SEQUENCE: 35

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
            85                  90                  95

Ile Ser Gly Ala Pro Asn Ser Asn Asp Gln Gly Thr Gly His Ile Leu
        100                 105                 110

His His Thr Ile Gly Lys Thr Asp Tyr Ser Tyr Gln Leu Glu Met Ala
    115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
            165                 170                 175

Arg Pro Gly Pro Val Ser Ser Leu Leu Ser Glu Pro Glu Ile Asp His
        180                 185                 190

Thr Ser Leu Lys Ala Ala Val Asp Ala Thr Val Ala Leu Leu Glu Lys
    195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Ala Lys Gly Phe Phe Pro Glu Asp His Ala Gly
            245                 250                 255

Phe Arg Gly Leu Tyr Trp Gly Glu Val Ser Asn Pro Gly Val Gln Glu
        260                 265                 270

Leu Val Glu Thr Ser Asp Ala Leu Leu Cys Ile Ala Pro Val Phe Asn
    275                 280                 285

Asp Tyr Ser Thr Val Gly Trp Ser Ala Trp Pro Lys Gly Pro Asn Val
            290                 295                 300
```

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
            325                 330                 335

Ala Arg Pro Ala Ser Ala Gln Lys Ser Ser Val Pro Thr Cys Ser Leu
        340                 345                 350

Thr Ala Thr Ser Asp Glu Ala Gly Leu Thr Asn Asp Glu Ile Val Arg
    355                 360                 365

His Ile Asn Ala Leu Leu Thr Ser Asn Thr Thr Leu Val Ala Glu Thr
370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
            405                 410                 415

Ser Ala Phe Gly Asn Ala Met Gly Ser Gln Asp Arg Gln His Val Val
        420                 425                 430

Met Val Gly Asp Gly Ser Phe Gln Leu Thr Ala Gln Glu Val Ala Gln
    435                 440                 445

Met Val Arg Tyr Glu Leu Pro Val Ile Ile Phe Leu Ile Asn Asn Arg
450                 455                 460

Gly Tyr Val Val Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
            485                 490                 495

Gly His Gly Leu Gly Leu Lys Ala Thr Thr Pro Lys Glu Leu Thr Glu
        500                 505                 510

Ala Ile Ala Arg Ala Lys Ala Asn Thr Arg Gly Pro Thr Leu Ile Glu
    515                 520                 525

Cys Gln Ile Asp Arg Thr Asp Cys Thr Asp Met Leu Val Gln His Gly
530                 535                 540

Arg Lys Val Ala Ser Thr Asn Ala Arg Lys Thr Thr Leu Ala Leu Glu
545                 550                 555                 560

<210> SEQ ID NO 36
<211> LENGTH: 560
<212> TYPE: PRT
<213> ORGANISM: Artificial Sequence
<220> FEATURE:
<223> OTHER INFORMATION: Synthetic

<400> SEQUENCE: 36

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
            85                  90                  95

Ile Ser Gly Ala Pro Asn Ser Asn Asp Gln Gly Thr Gly His Ile Leu
        100                 105                 110

-continued

His His Thr Ile Gly Lys Thr Asp Tyr Ser Tyr Gln Leu Glu Met Ala
            115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
                180                 185                 190

Thr Ser Leu Lys Ala Ala Val Asp Ala Thr Val Ala Leu Leu Glu Lys
            195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
                260                 265                 270

Leu Val Glu Thr Ser Asp Ala Leu Leu Cys Ile Ala Pro Val Phe Asn
            275                 280                 285

Asp Tyr Ser Thr Val Gly Trp Ser Ala Trp Pro Lys Gly Pro Asn Val
            290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
                340                 345                 350

Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
        370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
                420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
450                 455                 460

Gly Tyr Val Val Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Phe Gly

```
                    530                 535                 540
Arg Lys Val Ala Ser Thr Asn Ala Arg Lys Thr Thr Leu Ala Leu Glu
545                 550                 555                 560

<210> SEQ ID NO 37
<211> LENGTH: 560
<212> TYPE: PRT
<213> ORGANISM: Artificial Sequence
<220> FEATURE:
<223> OTHER INFORMATION: Synthetic

<400> SEQUENCE: 37

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
```

-continued

```
                    340                 345                 350
Thr Ala Thr Ser Asp Glu Ala Gly Leu Thr Asn Asp Glu Ile Val Arg
            355                 360                 365
His Ile Asn Ala Leu Leu Thr Ser Asn Thr Thr Leu Val Ala Glu Thr
        370                 375                 380
Gly Asp Ser Trp Phe Asn Ala Met Arg Met Thr Leu Pro Arg Gly Ala
385                 390                 395                 400
Arg Val Glu Leu Glu Met Gln Trp Gly His Ile Gly Trp Ser Val Pro
                405                 410                 415
Ser Ala Phe Gly Asn Ala Met Gly Ser Gln Asp Arg Gln His Val Val
            420                 425                 430
Met Val Gly Asp Gly Ser Phe Gln Leu Thr Ala Gln Glu Val Ala Gln
        435                 440                 445
Met Val Arg Tyr Glu Leu Pro Val Ile Ile Phe Leu Ile Asn Asn Arg
    450                 455                 460
Gly Tyr Val Val Gly Ile Ala Ile His Asp Gly Pro Tyr Asn Tyr Ile
465                 470                 475                 480
Lys Asn Trp Asp Tyr Ala Gly Leu Met Glu Val Phe Asn Ala Gly Glu
                485                 490                 495
Gly His Gly Leu Gly Leu Lys Ala Thr Thr Pro Lys Glu Leu Thr Glu
            500                 505                 510
Ala Ile Ala Arg Ala Lys Ala Asn Thr Arg Gly Pro Thr Leu Ile Glu
        515                 520                 525
Cys Gln Ile Asp Arg Thr Asp Cys Thr Asp Met Leu Val Gln Pro Gly
    530                 535                 540
Arg Lys Val Ala Ser Thr Asn Ala Arg Lys Thr Thr Leu Ala Leu Glu
545                 550                 555                 560

<210> SEQ ID NO 38
<211> LENGTH: 560
<212> TYPE: PRT
<213> ORGANISM: Artificial Sequence
<220> FEATURE:
<223> OTHER INFORMATION: Synthetic

<400> SEQUENCE: 38

Met Thr Tyr Thr Val Gly Met Tyr Leu Ala Glu Arg Leu Val Gln Ile
1               5                   10                  15
Gly Leu Lys His His Phe Ala Val Ala Gly Asp Tyr Asn Leu Val Leu
                20                  25                  30
Leu Asp Gln Leu Leu Leu Asn Lys Asp Met Lys Gln Ile Tyr Cys Cys
            35                  40                  45
Asn Glu Leu Asn Cys Gly Phe Ser Ala Glu Gly Tyr Ala Arg Ser Asn
        50                  55                  60
Gly Ala Ala Ala Ala Val Val Thr Phe Ser Val Gly Ala Ile Ser Ala
65                  70                  75                  80
Met Asn Ala Leu Gly Gly Ala Tyr Ala Glu Asn Leu Pro Val Ile Leu
                85                  90                  95
Ile Ser Gly Ala Pro Asn Ser Asn Asp Gln Gly Thr Gly His Ile Leu
            100                 105                 110
His His Thr Ile Gly Lys Thr Asp Tyr Ser Tyr Gln Leu Glu Met Ala
        115                 120                 125
Arg Gln Val Thr Cys Ala Ala Glu Ser Ile Thr Asp Ala His Ser Ala
    130                 135                 140
Pro Ala Lys Ile Asp His Val Ile Arg Thr Ala Leu Arg Glu Arg Lys
```

-continued

```
        145                 150                 155                 160
Pro Ala Tyr Leu Asp Ile Ala Cys Asn Ile Ala Ser Glu Pro Cys Val
                165                 170                 175
Arg Pro Gly Pro Val Ser Ser Leu Leu Ser Glu Pro Glu Ile Asp His
                180                 185                 190
Thr Ser Leu Lys Ala Ala Val Asp Ala Thr Val Ala Leu Leu Glu Lys
                195                 200                 205
Ser Ala Ser Pro Val Met Leu Leu Gly Ser Lys Leu Arg Ala Ala Asn
210                 215                 220
Ala Leu Ala Ala Thr Glu Thr Leu Ala Asp Lys Leu Gln Cys Ala Val
225                 230                 235                 240
Thr Ile Met Ala Ala Lys Gly Phe Phe Pro Glu Asp His Ala Gly
                245                 250                 255
Phe Arg Gly Leu Tyr Trp Gly Glu Val Ser Asn Pro Gly Val Gln Glu
                260                 265                 270
Leu Val Glu Thr Ser Asp Ala Leu Leu Cys Ile Ala Pro Val Phe Asn
                275                 280                 285
Asp Tyr Ser Thr Val Gly Trp Ser Ala Trp Pro Lys Gly Pro Asn Val
                290                 295                 300
Ile Leu Ala Glu Pro Asp Arg Val Thr Val Asp Gly Arg Ala Tyr Asp
305                 310                 315                 320
Gly Phe Thr Leu Arg Ala Phe Leu Gln Ala Leu Ala Glu Lys Ala Pro
                325                 330                 335
Ala Arg Pro Ala Ser Ala Gln Lys Ser Ser Val Pro Thr Cys Ser Leu
                340                 345                 350
Thr Ala Thr Ser Asp Glu Ala Gly Leu Thr Asn Asp Glu Ile Val Arg
                355                 360                 365
His Ile Asn Ala Leu Leu Thr Ser Asn Thr Thr Leu Val Ala Glu Thr
                370                 375                 380
Gly Asp Ser Trp Phe Asn Ala Met Arg Met Thr Leu Pro Arg Gly Ala
385                 390                 395                 400
Arg Val Glu Leu Glu Met Gln Trp Gly His Ile Gly Trp Ser Val Pro
                405                 410                 415
Ser Ala Phe Gly Asn Ala Met Gly Ser Gln Asp Arg Gln His Val Val
                420                 425                 430
Met Val Gly Asp Gly Ser Phe Gln Leu Thr Ala Gln Glu Val Ala Gln
                435                 440                 445
Met Val Arg Tyr Glu Leu Pro Val Ile Phe Leu Ile Asn Asn Arg
450                 455                 460
Gly Tyr Val Val Gly Ile Ala Ile His Asp Gly Pro Tyr Asn Tyr Ile
465                 470                 475                 480
Lys Asn Trp Asp Tyr Ala Gly Leu Met Glu Val Phe Asn Ala Gly Glu
                485                 490                 495
Gly His Gly Leu Gly Leu Lys Ala Thr Thr Pro Lys Glu Leu Thr Glu
                500                 505                 510
Ala Ile Ala Arg Ala Lys Ala Asn Thr Arg Gly Pro Thr Leu Ile Glu
                515                 520                 525
Cys Gln Ile Asp Arg Thr Asp Cys Thr Asp Met Leu Val Gln Ile Gly
                530                 535                 540
Arg Lys Val Ala Ser Thr Asn Ala Arg Lys Thr Thr Leu Ala Leu Glu
545                 550                 555                 560
```

<210> SEQ ID NO 39

<211> LENGTH: 560
<212> TYPE: PRT
<213> ORGANISM: Artificial Sequence
<220> FEATURE:
<223> OTHER INFORMATION: Synthetic

<400> SEQUENCE: 39

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
    290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
        355                 360                 365

His Ile Asn Ala Leu Leu Thr Ser Asn Thr Thr Leu Val Ala Glu Thr
    370                 375                 380
```

```
Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
            405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
450                 455                 460

Gly Tyr Val Val Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
            485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Leu Gly
530                 535                 540

Arg Lys Val Ala Ser Thr Asn Ala Arg Lys Thr Thr Leu Ala Leu Glu
545                 550                 555                 560

<210> SEQ ID NO 40
<211> LENGTH: 560
<212> TYPE: PRT
<213> ORGANISM: Artificial Sequence
<220> FEATURE:
<223> OTHER INFORMATION: Synthetic

<400> SEQUENCE: 40

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
50                  55                  60

Gly Ala Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
            115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190
```

```
Thr Ser Leu Lys Ala Ala Val Asp Ala Thr Val Ala Leu Leu Glu Lys
            195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
            245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
            275                 280                 285

Asp Tyr Ser Thr Val Gly Trp Ser Ala Trp Pro Lys Gly Pro Asn Val
            290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
            325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
            370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
            405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
            450                 455                 460

Gly Tyr Val Val Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
            485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Met Gly
            530                 535                 540

Arg Lys Val Ala Ser Thr Asn Ala Arg Lys Thr Thr Leu Ala Leu Glu
545                 550                 555                 560

<210> SEQ ID NO 41
<211> LENGTH: 560
<212> TYPE: PRT
<213> ORGANISM: Artificial Sequence
<220> FEATURE:
<223> OTHER INFORMATION: Synthetic

<400> SEQUENCE: 41
```

-continued

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
                35                  40                  45

Asn Glu Leu Asn Cys Gly Phe Ser Ala Glu Gly Tyr Ala Arg Ser Asn
        50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
                100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
        130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
                180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
                260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
        290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
                340                 345                 350

Thr Ala Thr Ser Asp Glu Ala Gly Leu Thr Asn Asp Glu Ile Val Arg
                355                 360                 365

His Ile Asn Ala Leu Leu Thr Ser Asn Thr Thr Leu Val Ala Glu Thr
        370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415
```

Ser Ala Phe Gly Asn Ala Met Gly Ser Gln Asp Arg Gln His Val Val
                420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
        450                 455                 460

Gly Tyr Val Val Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Val Gly
530                 535                 540

Arg Lys Val Ala Ser Thr Asn Ala Arg Lys Thr Thr Leu Ala Leu Glu
545                 550                 555                 560

<210> SEQ ID NO 42
<211> LENGTH: 560
<212> TYPE: PRT
<213> ORGANISM: Artificial Sequence
<220> FEATURE:
<223> OTHER INFORMATION: Synthetic

<400> SEQUENCE: 42

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
            245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
            275                 280                 285

Asp Tyr Ser Thr Val Gly Trp Ser Ala Trp Pro Lys Gly Pro Asn Val
            290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
            325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
            405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
450                 455                 460

Gly Tyr Val Val Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
            485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Ala Gly
530                 535                 540

Arg Lys Val Ala Ser Thr Asn Ala Arg Lys Thr Thr Leu Ala Leu Glu
545                 550                 555                 560

<210> SEQ ID NO 43
<211> LENGTH: 560
<212> TYPE: PRT
<213> ORGANISM: Artificial Sequence
<220> FEATURE:
<223> OTHER INFORMATION: Synthetic

<400> SEQUENCE: 43

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

-continued

```
Leu Asp Gln Leu Leu Leu Asn Lys Asp Met Lys Gln Ile Tyr Cys Cys
         35                  40                  45

Asn Glu Leu Asn Cys Gly Phe Ser Ala Glu Gly Tyr Ala Arg Ser Asn
 50                  55                  60

Gly Ala Ala Ala Val Val Thr Phe Ser Val Gly Ala Ile Ser Ala
 65              70                  75                  80

Met Asn Ala Leu Gly Gly Ala Tyr Ala Glu Asn Leu Pro Val Ile Leu
                 85                  90                  95

Ile Ser Gly Ala Pro Asn Ser Asn Asp Gln Gly Thr Gly His Ile Leu
             100                 105                 110

His His Thr Ile Gly Lys Thr Asp Tyr Ser Tyr Gln Leu Glu Met Ala
         115                 120                 125

Arg Gln Val Thr Cys Ala Ala Glu Ser Ile Thr Asp Ala His Ser Ala
     130                 135                 140

Pro Ala Lys Ile Asp His Val Ile Arg Thr Ala Leu Arg Glu Arg Lys
 145                 150                 155                 160

Pro Ala Tyr Leu Asp Ile Ala Cys Asn Ile Ala Ser Glu Pro Cys Val
                 165                 170                 175

Arg Pro Gly Pro Val Ser Ser Leu Leu Ser Glu Pro Glu Ile Asp His
             180                 185                 190

Thr Ser Leu Lys Ala Ala Val Asp Ala Thr Val Ala Leu Leu Glu Lys
         195                 200                 205

Ser Ala Ser Pro Val Met Leu Leu Gly Ser Lys Leu Arg Ala Ala Asn
     210                 215                 220

Ala Leu Ala Ala Thr Glu Thr Leu Ala Asp Lys Leu Gln Cys Ala Val
 225                 230                 235                 240

Thr Ile Met Ala Ala Lys Gly Phe Phe Pro Glu Asp His Ala Gly
                 245                 250                 255

Phe Arg Gly Leu Tyr Trp Gly Glu Val Ser Asn Pro Gly Val Gln Glu
             260                 265                 270

Leu Val Glu Thr Ser Asp Ala Leu Leu Cys Ile Ala Pro Val Phe Asn
         275                 280                 285

Asp Tyr Ser Thr Val Gly Trp Ser Ala Trp Pro Lys Gly Pro Asn Val
     290                 295                 300

Ile Leu Ala Glu Pro Asp Arg Val Thr Val Asp Gly Arg Ala Tyr Asp
 305                 310                 315                 320

Gly Phe Thr Leu Arg Ala Phe Leu Gln Ala Leu Ala Glu Lys Ala Pro
                 325                 330                 335

Ala Arg Pro Ala Ser Ala Gln Lys Ser Ser Val Pro Thr Cys Ser Leu
             340                 345                 350

Thr Ala Thr Ser Asp Glu Ala Gly Leu Thr Asn Asp Glu Ile Val Arg
         355                 360                 365

His Ile Asn Ala Leu Leu Thr Ser Asn Thr Thr Leu Val Ala Glu Thr
     370                 375                 380

Gly Asp Ser Trp Phe Asn Ala Met Arg Met Thr Leu Pro Arg Gly Ala
 385                 390                 395                 400

Arg Val Glu Leu Glu Met Gln Trp Gly His Ile Gly Trp Ser Val Pro
                 405                 410                 415

Ser Ala Phe Gly Asn Ala Met Gly Ser Gln Asp Arg Gln His Val Val
             420                 425                 430

Met Val Gly Asp Gly Ser Phe Gln Leu Thr Ala Gln Glu Val Ala Gln
         435                 440                 445

Met Val Arg Tyr Glu Leu Pro Val Ile Ile Phe Leu Ile Asn Asn Arg
```

```
            450                 455                 460
Gly Tyr Val Val Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Tyr Gly
            530                 535                 540

Arg Lys Val Ala Ser Thr Asn Ala Arg Lys Thr Thr Leu Ala Leu Glu
545                 550                 555                 560
```

<210> SEQ ID NO 44
<211> LENGTH: 560
<212> TYPE: PRT
<213> ORGANISM: Artificial Sequence
<220> FEATURE:
<223> OTHER INFORMATION: Synthetic

<400> SEQUENCE: 44

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
                20                  25                  30

Leu Asp Gln Leu Leu Leu Asn Lys Asp Met Lys Gln Ile Tyr Cys Cys
            35                  40                  45

Asn Glu Leu Asn Cys Gly Phe Ser Ala Glu Gly Tyr Ala Arg Ser Asn
        50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
```

```
            260                 265                 270
Leu Val Glu Thr Ser Asp Ala Leu Leu Cys Ile Ala Pro Val Phe Asn
                275                 280                 285

Asp Tyr Ser Thr Val Gly Trp Ser Ala Trp Pro Lys Gly Pro Asn Val
            290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
            370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
450                 455                 460

Gly Tyr Val Val Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Thr Gly
            530                 535                 540

Arg Lys Val Ala Ser Thr Asn Ala Arg Lys Thr Thr Leu Ala Leu Glu
545                 550                 555                 560
```

<210> SEQ ID NO 45
<211> LENGTH: 560
<212> TYPE: PRT
<213> ORGANISM: Artificial Sequence
<220> FEATURE:
<223> OTHER INFORMATION: Synthetic

<400> SEQUENCE: 45

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Ala Val Val Thr Phe Ser Val Gly Ala Ile Ser Ala
```

```
                65                  70                  75                  80
        Met Asn Ala Leu Gly Gly Ala Tyr Ala Glu Asn Leu Pro Val Ile Leu
                            85                  90                  95

Ile Ser Gly Ala Pro Asn Ser Asn Asp Gln Gly Thr Gly His Ile Leu
                        100                 105                 110

His His Thr Ile Gly Lys Thr Asp Tyr Ser Tyr Gln Leu Glu Met Ala
                        115                 120                 125

Arg Gln Val Thr Cys Ala Ala Glu Ser Ile Thr Asp Ala His Ser Ala
                    130                 135                 140

Pro Ala Lys Ile Asp His Val Ile Arg Thr Ala Leu Arg Glu Arg Lys
        145                 150                 155                 160

Pro Ala Tyr Leu Asp Ile Ala Cys Asn Ile Ala Ser Glu Pro Cys Val
                            165                 170                 175

Arg Pro Gly Pro Val Ser Ser Leu Leu Ser Glu Pro Glu Ile Asp His
                        180                 185                 190

Thr Ser Leu Lys Ala Ala Val Asp Ala Thr Val Ala Leu Leu Glu Lys
                        195                 200                 205

Ser Ala Ser Pro Val Met Leu Leu Gly Ser Lys Leu Arg Ala Ala Asn
                    210                 215                 220

Ala Leu Ala Ala Thr Glu Thr Leu Ala Asp Lys Leu Gln Cys Ala Val
        225                 230                 235                 240

Thr Ile Met Ala Ala Ala Lys Gly Phe Phe Pro Glu Asp His Ala Gly
                            245                 250                 255

Phe Arg Gly Leu Tyr Trp Gly Glu Val Ser Asn Pro Gly Val Gln Glu
                        260                 265                 270

Leu Val Glu Thr Ser Asp Ala Leu Leu Cys Ile Ala Pro Val Phe Asn
                        275                 280                 285

Asp Tyr Ser Thr Val Gly Trp Ser Ala Trp Pro Lys Gly Pro Asn Val
                    290                 295                 300

Ile Leu Ala Glu Pro Asp Arg Val Thr Val Asp Gly Arg Ala Tyr Asp
        305                 310                 315                 320

Gly Phe Thr Leu Arg Ala Phe Leu Gln Ala Leu Ala Glu Lys Ala Pro
                            325                 330                 335

Ala Arg Pro Ala Ser Ala Gln Lys Ser Ser Val Pro Thr Cys Ser Leu
                        340                 345                 350

Thr Ala Thr Ser Asp Glu Ala Gly Leu Thr Asn Asp Glu Ile Val Arg
                        355                 360                 365

His Ile Asn Ala Leu Leu Thr Ser Asn Thr Thr Leu Val Ala Glu Thr
                    370                 375                 380

Gly Asp Ser Trp Phe Asn Ala Met Arg Met Thr Leu Pro Arg Gly Ala
        385                 390                 395                 400

Arg Val Glu Leu Glu Met Gln Trp Gly His Ile Gly Trp Ser Val Pro
                            405                 410                 415

Ser Ala Phe Gly Asn Ala Met Gly Ser Gln Asp Arg Gln His Val Val
                        420                 425                 430

Met Val Gly Asp Gly Ser Phe Gln Leu Thr Ala Gln Glu Val Ala Gln
                        435                 440                 445

Met Val Arg Tyr Glu Leu Pro Val Ile Ile Phe Leu Ile Asn Asn Arg
                    450                 455                 460

Gly Tyr Val Val Gly Ile Ala Ile His Asp Gly Pro Tyr Asn Tyr Ile
        465                 470                 475                 480

Lys Asn Trp Asp Tyr Ala Gly Leu Met Glu Val Phe Asn Ala Gly Glu
                            485                 490                 495
```

```
Gly His Gly Leu Gly Leu Lys Ala Thr Thr Pro Lys Glu Leu Thr Glu
                500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Gly Gly
530                 535                 540

Arg Lys Val Ala Ser Thr Asn Ala Arg Lys Thr Thr Leu Ala Leu Glu
545                 550                 555                 560

<210> SEQ ID NO 46
<211> LENGTH: 560
<212> TYPE: PRT
<213> ORGANISM: Artificial Sequence
<220> FEATURE:
<223> OTHER INFORMATION: Synthetic

<400> SEQUENCE: 46

Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
290                 295                 300
```

```
Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
            325                 330                 335

Ala Arg Pro Ala Ser Ala Gln Lys Ser Ser Val Pro Thr Cys Ser Leu
        340                 345                 350

Thr Ala Thr Ser Asp Glu Ala Gly Leu Thr Asn Asp Glu Ile Val Arg
    355                 360                 365

His Ile Asn Ala Leu Leu Thr Ser Asn Thr Thr Leu Val Ala Glu Thr
370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
        435                 440                 445

Met Val Arg Tyr Glu Leu Pro Val Ile Ile Phe Leu Ile Asn Asn Arg
    450                 455                 460

Gly Tyr Val Val Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
        515                 520                 525

Cys Gln Ile Asp Arg Thr Asp Cys Thr Asp Met Leu Val Gln Ser Gly
    530                 535                 540

Arg Lys Val Ala Ser Thr Asn Ala Arg Lys Thr Thr Leu Ala Leu Glu
545                 550                 555                 560
```

<210> SEQ ID NO 47
<211> LENGTH: 560
<212> TYPE: PRT
<213> ORGANISM: Artificial Sequence
<220> FEATURE:
<223> OTHER INFORMATION: Synthetic

<400> SEQUENCE: 47

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110
```

-continued

```
His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Ser Glu Pro Glu Ile Asp His
                180                 185                 190

Thr Ser Leu Lys Ala Ala Val Asp Ala Thr Val Ala Leu Leu Glu Lys
                195                 200                 205

Ser Ala Ser Pro Val Met Leu Leu Gly Ser Lys Leu Arg Ala Ala Asn
210                 215                 220

Ala Leu Ala Ala Thr Glu Thr Leu Ala Asp Lys Leu Gln Cys Ala Val
225                 230                 235                 240

Thr Ile Met Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
                260                 265                 270

Leu Val Glu Thr Ser Asp Ala Leu Leu Cys Ile Ala Pro Val Phe Asn
            275                 280                 285

Asp Tyr Ser Thr Val Gly Trp Ser Ala Trp Pro Lys Gly Pro Asn Val
            290                 295                 300

Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
            370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
            420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
450                 455                 460

Gly Tyr Val Val Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
            515                 520                 525
```

```
Cys Gln Ile Asp Arg Thr Asp Cys Thr Asp Met Leu Val Gln Cys Gly
    530                 535                 540
Arg Lys Val Ala Ser Thr Asn Ala Arg Lys Thr Thr Leu Ala Leu Glu
545                 550                 555                 560
```

<210> SEQ ID NO 48
<211> LENGTH: 1680
<212> TYPE: DNA
<213> ORGANISM: Artificial Sequence
<220> FEATURE:
<223> OTHER INFORMATION: Synthetic

<400> SEQUENCE: 48

```
atgacctata ctgttggcat gtatcttgca gaacgccttg tacagatcgg gctgaagcat      60
cacttcgccg tggcgggcga ctacaatctc gttcttctgg atcagttgct cctcaacaag     120
gacatgaaac agatctattg ctgcaatgag ttgaactgtg gcttcagcgc ggaaggctac     180
gcccgttcta cggggctgc ggcagcggtt gtcaccttca gcgttggcgc catttccgcc     240
atgaacgccc tcgcggcgc ctatgccgaa aacctgccgg ttatcctgat ttccggcgcg     300
cccaacagca tgatcaggg cacaggtcat atcctgcatc acacaatcgg caagacggat     360
tacagctacc agcttgaaat ggcccgtcag gtcacctgtg ccgccgaaag cattaccgac     420
gctcactccg ccccggccaa gattgaccac gtcattcgca cggcgctgcg cgagcgtaag     480
ccggcctatc tggacatcgc gtgcaacatt gcctccgagc cctgcgtgcg gcctggccct     540
gtcagcagcc tgctgtccga gcctgaaatc gaccacacga gcctgaaggc cgcagtggac     600
gccacggttg ccttgctgga aaaatcggcc agccccgtca tgctgctggg cagcaagctg     660
cgggccgcca cgcactggc cgcaaccgaa acgctggcag acaagctgca atgcgcggtg     720
accatcatgg cggccgcgaa aggctttttc cccgaagacc acgcgggttt ccgcggcctg     780
tactggggcg aagtctcgaa ccccggcgtg caggaactgg tggagacctc cgacgcactg     840
ctgtgcatcg cccccgtatt caacgactat tcaacagtcg gctggtcggc atggcccaag     900
ggccccaatg tgattctggc tgagcccgac cgcgtaacgg tcgatggccg cgcctatgac     960
ggctttaccc tgcgcgcctt cctgcaggct ctggcggaaa agcccccgc gcgcccggcc    1020
tccgcacaga aaagcagcgt cccgacgtgc tcgctcaccg cgacatccga tgaagccggt    1080
ctgacgaatg acgaaatcgt ccgtcatatc aacgccctgc tgacatcaaa cacgacgctg    1140
gtggcagaaa ccggcgattc atggttcaat gccatgcgca tgaccctgcc cgcgcggtgcg    1200
cgcgtggaac tggaaatgca gtggggccat atcggctggt ccgtgccctc cgccttcggc    1260
aatgccatgg gctcgcagga ccgccagcat gtggtgatgg taggcgatgg ctccttccag    1320
cttaccgcgc aggaagtggc tcagatggtg cgctacgaac tgcccgtcat tatctttctg    1380
atcaacaacc gtggctatgt cgccggcatc gccattcatg acggcccgta caactatatc    1440
aagaactggg attacgccgg cctgatggaa gtcttcaacg ccggagaagg ccatggactt    1500
ggcctgaaag ccaccacccc gaaggaactg acagaagcca tcgccagggc aaaagccaat    1560
acccgcggcc cgacgctgat cgaatgccag atcgaccgca cggactgcac ggatatgctg    1620
gttcaatttg ccgcaaggt tgcctcaacc aacgcgcgca agaccactct ggccctcgag    1680
```

<210> SEQ ID NO 49
<211> LENGTH: 7041
<212> TYPE: DNA
<213> ORGANISM: Artificial Sequence
<220> FEATURE:
<223> OTHER INFORMATION: Synthetic

<400> SEQUENCE: 49

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tcccttagg      180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taggggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg agacaataac cctgataaat gcttcaataa tattgaaaaa ggaagagtat     600
gagtattcaa catttccgtg tcgcccttat cccttttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca caacatgggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct taacgtgagt tttcgttcca ctgagcgtca gaccccgtag aaaagatcaa    1620
aggatcttct tgagatcctt ttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcgg agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggcctttt tacggttcct ggccttttgc tggccttttg ctcacatgtt    2280
```

```
ctttcctgcg ttatcccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaaggggg atttctgttc atggggtaa     2880 tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt tggtggcgg     3360 gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagcaga    4140 cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga ataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg caacgccaa tcagcaacga ctgtttgccc     4560
gccagttgtt gtgccacgcg gttgggaatg taattcagct ccgccatcgc cgcttccact    4620
tttcccgcgt ttttcgcaga aacgtggctg gcctggttca ccacgcggga aacggtctga    4680
```

```
taagagacac cggcatactc tgcgacatcg tataacgtta ctggtttcac attcaccacc   4740
ctgaattgac tctcttccgg gcgctatcat gccataccgc gaaaggtttt gcgccattcg   4800
atggtgtccg ggatctcgac gctctcccdtt atgcgactcc tgcattagga agcagcccag   4860
tagtaggttg aggccgttga gcaccgccgc cgcaaggaat ggtgcatgca aggagatggc   4920
gcccaacagt cccccggcca cggggcctgc caccataccc acgccgaaac aagcgctcat   4980
gagcccgaag tggcgagccc gatcttcccc atcggtgatg tcggcgatat aggcgccagc   5040
aaccgcacct gtggcgccgg tgatgccggc cacgatgcgt ccggcgtaga ggatcgagat   5100
ctcgatcccg cgaaattaat acgactcact atagggaat tgtgagcgga taacaattcc   5160
cctctagaaa taattttgtt aactttaag aaggagatat acatatgacc tatactgttg   5220
gcatgtatct tgcagaacgc cttgtacaga tcgggctgaa gcatcacttc gccgtggcgg   5280
gcgactacaa tctcgttctt ctggatcagt tgctcctcaa caaggacatg aaacagatct   5340
attgctgcaa tgagttgaac tgtggcttca gcgcggaagg ctacgcccgt tctaacgggg   5400
ctgcggcagc ggttgtcacc ttcagcgttg gcgccatttc cgccatgaac gccctcggcg   5460
gcgcctatgc cgaaaacctg ccggttatcc tgatttccgg cgcgcccaac agcaatgatc   5520
agggcacagg tcatatcctg catcacacaa tcggcaagac ggattacagc taccagcttg   5580
aaatggcccg tcaggtcacc tgtgccgccg aaagcattac cgacgctcac tccgccccgg   5640
ccaagattga ccacgtcatt cgcacggcgc tgcgcgagcg taagccggcc tatctggaca   5700
tcgcgtgcaa cattgcctcc gagccctgcg tgcggcctgg ccctgtcagc agcctgctgt   5760
ccgagcctga aatcgaccac acgagcctga aggccgcagt ggacgccacg gttgccttgc   5820
tggaaaaatc ggccagcccc gtcatgctgc tgggcagcaa gctgcgggcc gccaacgcac   5880
tggccgcaac cgaaacgctg gcagacaagc tgcaatgcgc ggtgaccatc atggcggccg   5940
cgaaaggctt ttttccccgaa gaccacgcgg gtttccgcgg cctgtactgg ggcgaagtct   6000
cgaaccccgg cgtgcaggaa ctggtggaga cctccgacgc actgctgtgc atcgcccccg   6060
tattcaacga ctattcaaca gtcggctggt cggcatggcc caagggcccc aatgtgattc   6120
tggctgagcc cgaccgcgta acggtcgatg ccgcgcccta tgacggcttt accctgcgcg   6180
ccttcctgca ggctctggcg gaaaaagccc ccgcgcgccc ggcctccgca cagaaaagca   6240
gcgtcccgac gtgctcgctc accgcgacat ccgatgaagc cggtctgacg aatgacgaaa   6300
tcgtccgtca tatcaacgcc ctgctgacat caaacacgac gctggtggca gaaaccggcg   6360
attcatggtt caatgccatg cgcatgaccc tgccgcgcgg tgcgcgcgtg gaactggaaa   6420
tgcagtgggg ccatatcggc tggtccgtgc cctccgcctt cggcaatgcc atgggctcgc   6480
aggaccgcca gcatgtggtg atggtaggcg atggctcctt ccagcttacc gcgcaggaag   6540
tggctcagat ggtgcgctac gaactgcccg tcattatctt tctgatcaac aaccgtggct   6600
atgtcgccgg catcgccatt catgacggcc cgtacaacta tatcaagaac tgggattacg   6660
ccggcctgat ggaagtcttc aacgccggag aaggccatgg acttggcctg aaagccacca   6720 cccccgaagga actgacagaa gccatcgcca gggcaaaagc caatacccgc ggcccgacgc   6780
tgatcgaatg ccagatcgac cgcacggact gcacggatat gctggttcaa tttgccgca   6840 aggttgcctc aaccaacgcg cgcaagacca ctctggccct cgagcaccac caccaccacc   6900
actgagatcc ggctgctaac aaagcccgaa aggaagctga gttggctgct gccaccgctg   6960
agcaataact agcataaccc cttggggcct ctaaacgggt cttgaggggt ttttgctga    7020
```
aaggaggaac tatatccgga t                                              7041

<210> SEQ ID NO 50
<211> LENGTH: 34
<212> TYPE: DNA
<213> ORGANISM: Artificial Sequence
<220> FEATURE:
<223> OTHER INFORMATION: Synthetic

<400> SEQUENCE: 50
accttgcggc cgaattgaac cagcatatcc gtgc                                  34

<210> SEQ ID NO 51
<211> LENGTH: 34
<212> TYPE: DNA
<213> ORGANISM: Artificial Sequence
<220> FEATURE:
<223> OTHER INFORMATION: Synthetic

<400> SEQUENCE: 51
gcacggatat gctggttcaa ttcggccgca aggt                                  34

<210> SEQ ID NO 52
<211> LENGTH: 1680
<212> TYPE: DNA
<213> ORGANISM: Artificial Sequence
<220> FEATURE:
<223> OTHER INFORMATION: Synthetic

<400> SEQUENCE: 52
atgacctata ctgttggcat gtatcttgca gaacgccttg tacagatcgg gctgaagcat        60
cacttcgccg tggcgggcga ctacaatctc gttcttctgg atcagttgct cctcaacaag       120
gacatgaaac agatctattg ctgcaatgag ttgaactgtg gcttcagcgc ggaaggctac       180
gcccgttcta acggggctgc ggcagcggtt gtcaccttca gcgttggcgc catttccgcc       240
atgaacgccc tcggcggcgc ctatgccgaa aacctgccgg ttatcctgat tccggcgcg        300 cccaacagca atgatcaggg cacaggtcat atcctgcatc acacaatcgg caagacggat       360
tacagctacc agcttgaaat ggcccgtcag gtcacctgtg ccgccgaaag cattaccgac       420
gctcactccg ccccggccaa gattgaccac gtcattcgca cggcgctgcg cgagcgtaag       480
ccggcctatc tggacatcgc gtgcaacatt gcctccgagc cctgcgtgcg gcctggccct       540
gtcagcagcc tgctgtccga gcctgaaatc gaccacacga gcctgaaggc cgcagtggac       600
gccacggttg ccttgctgga aaaatcggcc agccccgtca tgctgctggg cagcaagctg       660
cgggccgcca acgcactggc cgcaaccgaa acgctggcag acaagctgca atgcgcggtg       720
accatcatgg cggccgcgaa aggctttttc cccgaagacc acgcgggttt ccgcggcctg       780
tactggggcg aagtctcgaa ccccggcgtg caggaactgg tggagacctc cgacgcactg       840
ctgtgcatcg cccccgtatt caacgactat tcaacagtcg gctggtcggc atggcccaag       900
ggccccaatg tgattctggc tgagcccgac cgcgtaacgg tcgatggccg cgcctatgac       960
ggctttaccc tgcgcgcctt cctgcaggct ctggcggaaa agcccccgc gcgcccggcc      1020 tccgcacaga aaagcagcgt cccgacgtgc tcgctcaccg cgacatccga tgaagccggt      1080
ctgacgaatg acgaaatcgt ccgtcatatc aacgccctgc tgacatcaaa cacgacgctg      1140
gtggcagaaa ccggcgattc atggttcaat gccatgcgca tgaccctgcc gcgcggtgcg      1200
cgcgtggaac tggaaatgca gtggggccat atcggctggt ccgtgccctc cgccttcggc      1260
aatgccatgg gctcgcagga ccgccagcat gtggtgatgg taggcgatgg ctccttccag      1320

```
cttaccgcgc aggaagtggc tcagatggtg cgctacgaac tgcccgtcat tatctttctg   1380
atcaacaacc gtggctatgt cgccggcatc gccattcatg acggcccgta caactatatc   1440
aagaactggg attacgccgg cctgatggaa gtcttcaacg ccggagaagg ccatggactt   1500
ggcctgaaag ccaccacccc gaaggaactg acagaagcca tcgccagggc aaaagccaat   1560
acccgcggcc cgacgctgat cgaatgccag atcgaccgca cggactgcac ggatatgctg   1620
gttcaatggg gccgcaaggt tgcctcaacc aacgcgcgca agaccactct ggccctcgag   1680
```

<210> SEQ ID NO 53
<211> LENGTH: 560
<212> TYPE: PRT
<213> ORGANISM: Artificial Sequence
<220> FEATURE:
<223> OTHER INFORMATION: Synthetic

<400> SEQUENCE: 53

```
Met Thr Tyr Thr Val Gly Met Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Gln Leu Leu Leu Asn Lys Asp Met Lys Gln Ile Tyr Cys Cys
        35                  40                  45

Asn Glu Leu Asn Cys Gly Phe Ser Ala Glu Gly Tyr Ala Arg Ser Asn
    50                  55                  60

Gly Ala Ala Ala Val Val Thr Phe Ser Val Gly Ala Ile Ser Ala
65                  70                  75                  80

Met Asn Ala Leu Gly Gly Ala Tyr Ala Glu Asn Leu Pro Val Ile Leu
                85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Glu Lys
        195                 200                 205

Ser Ala Ser Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240

Thr Ile Met Ala Ala Ala Lys Gly Phe Phe Pro Glu Asp His Ala Gly
                245                 250                 255

Phe Arg Gly Leu Tyr Trp Gly Glu Val Ser Asn Pro Gly Val Gln Glu
            260                 265                 270

Leu Val Glu Thr Ser Asp Ala Leu Leu Cys Ile Ala Pro Val Phe Asn
        275                 280                 285

Asp Tyr Ser Thr Val Gly Trp Ser Ala Trp Pro Lys Gly Pro Asn Val
    290                 295                 300
```

-continued

```
Ile Leu Ala Glu Pro Asp Arg Val Thr Val Asp Gly Arg Ala Tyr Asp
305                 310                 315                 320

Gly Phe Thr Leu Arg Ala Phe Leu Gln Ala Leu Ala Glu Lys Ala Pro
                325                 330                 335

Ala Arg Pro Ala Ser Ala Gln Lys Ser Ser Val Pro Thr Cys Ser Leu
            340                 345                 350

Thr Ala Thr Ser Asp Glu Ala Gly Leu Thr Asn Asp Glu Ile Val Arg
            355                 360                 365

His Ile Asn Ala Leu Leu Thr Ser Asn Thr Thr Leu Val Ala Glu Thr
            370                 375                 380

Gly Asp Ser Trp Phe Asn Ala Met Arg Met Thr Leu Pro Arg Gly Ala
385                 390                 395                 400

Arg Val Glu Leu Glu Met Gln Trp Gly His Ile Gly Trp Ser Val Pro
                405                 410                 415

Ser Ala Phe Gly Asn Ala Met Gly Ser Gln Asp Arg Gln His Val Val
                420                 425                 430

Met Val Gly Asp Gly Ser Phe Gln Leu Thr Ala Gln Glu Val Ala Gln
            435                 440                 445

Met Val Arg Tyr Glu Leu Pro Val Ile Ile Phe Leu Ile Asn Asn Arg
            450                 455                 460

Gly Tyr Val Ile Gly Ile Ala Ile His Asp Gly Pro Tyr Asn Tyr Ile
465                 470                 475                 480

Lys Asn Trp Asp Tyr Ala Gly Leu Met Glu Val Phe Asn Ala Gly Glu
                485                 490                 495

Gly His Gly Leu Gly Leu Lys Ala Thr Thr Pro Lys Glu Leu Thr Glu
            500                 505                 510

Ala Ile Ala Arg Ala Lys Ala Asn Thr Arg Gly Pro Thr Leu Ile Glu
            515                 520                 525

Cys Gln Ile Asp Arg Thr Asp Cys Thr Asp Met Leu Val Gln Trp Gly
            530                 535                 540

Arg Lys Val Ala Ser Thr Asn Ala Arg Lys Thr Thr Leu Ala Leu Glu
545                 550                 555                 560
```